(12) United States Patent
Mattes et al.

(10) Patent No.: US 6,884,611 B2
(45) Date of Patent: Apr. 26, 2005

(54) PREPARATION OF ACARIOGENIC SUGAR SUBSTITUTES

(75) Inventors: Ralf Mattes, Stuttgart (DE); Kathrin Klein, Stuttgart (DE); Hurbert Schiweck, Worms (DE); Markwart Kunz, Worms (DE); Mohammed Munir, Kindenheim (DE)

(73) Assignee: Sudzucker Aktiengesellschaft, Mannheim /Ochsenfurt (DE)

( * ) Notice: Subject to any disclaimer, the term of this patent is extended or adjusted under 35 U.S.C. 154(b) by 0 days.

(21) Appl. No.: 10/061,269

(22) Filed: Feb. 4, 2002

(65) Prior Publication Data

US 2003/0087416 A1 May 8, 2003

Related U.S. Application Data

(60) Continuation-in-part of application No. 09/168,720, filed on Oct. 9, 1998, now abandoned, which is a division of application No. 08/785,396, filed on Jan. 21, 1997, now Pat. No. 5,985,622, which is a division of application No. 08/374,155, filed on Jan. 18, 1995, now Pat. No. 5,786,140.

(30) Foreign Application Priority Data

Jan. 19, 1994 (DE) .................................. P 44 01 451
Apr. 22, 1994 (DE) .................................. 44 14 185

(51) Int. Cl.$^7$ ........................... C12P 21/06; C12N 9/00; C12N 9/90; C12N 1/20; C07H 21/04

(52) U.S. Cl. ............................. 435/233; 435/4; 435/6; 435/69.1; 435/183; 435/252.3; 435/252.33; 435/320.1; 536/23.2; 536/23.4; 536/23.7

(58) Field of Search ......................... 435/4, 6, 69.1, 435/183, 233, 252.3, 252.8, 252.33, 320.1; 536/23.2, 23.4, 23.7, 23.74

(56) References Cited

U.S. PATENT DOCUMENTS

| | | | |
|---|---|---|---|
| 4,359,531 A | 11/1982 | Bucke et al. ................. | 435/97 |
| 4,390,627 A | 6/1983 | Lantero, Jr. ................. | 435/180 |
| 4,670,387 A | 6/1987 | Bucke et al. ................. | 435/97 |
| 4,788,145 A | 11/1988 | Munir ........................ | 435/100 |
| 4,857,461 A | 8/1989 | Egerer et al. ................ | 435/94 |
| 5,229,276 A | 7/1993 | Sugitani et al. .............. | 435/97 |
| 5,336,617 A | 8/1994 | Sugitani et al. ............. | 435/252.1 |

FOREIGN PATENT DOCUMENTS

| | | |
|---|---|---|
| EP | 0 109 009 A1 | 5/1980 |
| EP | 0 028 900 A1 | 5/1981 |
| EP | 0 200 069 A2 | 12/1986 |
| EP | 0 483 755 A2 | 5/1992 |
| JP | 3-160995 | 7/1991 |
| JP | 4-169190 | 6/1992 |
| WO | WO 92/10580 | 6/1992 |

OTHER PUBLICATIONS

Ausubel et al (Current Protocols in Molecular Biology, vols. 1 and II, 1989.*
Nakajima, Y.J., "Manufacture and Utilization of Palatinose" Jpn. Soc. Starch Sci., 35:131–139 (1988).
Tsuyuki K. et al. "Isolation and Characterization of Isomaltulose– and Trehalulose–Producing Bacteria From Thailand Soil," J. Gen. Appl. Microbiol. 38:483–490, Jul. 2, 1992.
Joklik, W., et al., "Enterobacteriaceae: General Characteristics," *Zinsser Microbiology*, 18th Ed., pp. 595–601, 1968.
Lizuka, M., et al., "Susceptibility of leucrose to carbohydrases," *Biological Abstracts*, Jun. 1991.
Miyata, Y. et al. "Isolation and characterization of *Pseudomonas mesoacidophila* producing trehalulose" *Bioscience, Biotechnology, and Biochemistry,* 56(10):1680–1681, Oct. 1992.
Nagai, Y. et al., "Characterization of α–Glucosyltransferase from *Pseudomonas mesoacidophila* MX–45" *Biosci. Biotech. Biochem*, 58(10):1789–1793, 1994.
Sprenger, G., and Lengeler, J., "Analysis of Sucrose Catabolism in *Klebsiella pneumoniae* and in Scr+ Derivatives of *Escherichia coli* K 12," J. Gen. Micorbiology, 134:1635–1644, 1988.
Bockmann, J. et al., "Characterization of a chomosomaly encoded, non–PTS metabolic pathway for sucrose utilization in *Escherichia coli* EC3132," *Mol Gen Genet*, 235:22–32 (1992).
Brock, T.D., et al., "Kinds of Plasmids and Their Biological Significance," *Biology of Micro–Organisms*, Prentice–Hall, Inc., Chapter 8, Section 7.6–7.9, pp. 278–314, 1988.
Bugaenko, I.F., "Sweetening substances on the basis of sucrose," *Chemical Abstracts*, 1993–1994.
Cheetam, P.S.J. (1984) "The extraction and mechanism of a novel isomaltulose–synthesizing enzyme from *Erwini rhapontici,"* Biochem. J., 220:213–220.
Cheetham, P.S.J. et al. "The formation of isomaltulose by immobilized *Erwinia rhapontici,"* Nature 299:628–631, Oct. 14, 1982.
Crabb, W.D., et al., "Tools and Strategies for Cloning Studies," in Streips and Yasbin *Modern Microbial Genetics*, pp. 365–388, 1991.
Ernst–Ludwig Winnacker, "From Genes to Clones: Introduction to Gene Technology," Weinhem (Federal Republic of Germany): VCH Verlagsgesellschaft (1987) pp. 383–395.
Hartmeier, W., "Immobilized Biocatalysts: An Introduction," *Springer–Verlag*, pp. 139–144 (1986).
Ioroi, R., et al., "Oligosaccharide Production by Dextransucrase of *Streptococcus bovis* No. 148 Isolated from Bovine Rumen," *Nippon Shokuhin Kogyo Gakkaishi*, 37(5):355–362 (1990).

(Continued)

*Primary Examiner*—Manjunath N. Rao
(74) *Attorney, Agent, or Firm*—Finnegan, Henderson, Farabow, Garrett & Dunner, LLP

(57) ABSTRACT

The invention relates to sucrose isomerases, to DNA sequences that code for sucrose isomerases, and to novel processes for the production of non-cariogenic sugars.

9 Claims, 6 Drawing Sheets

OTHER PUBLICATIONS

Itoh, Y., et al., "Synthesis of Leucrose by Dextransucrase and Some Conditions for the Reaction," *Nippon Shokuhin Kogyo Gakkaishi*, 37(3):171–177, 1990.

Jahreis, K. and Lengeler, J., "Molecular analysis of two ScrR repressors and of a ScrR–FruR hybrid repressor for sucrose and D–Frutose specific regulons from enteric bacteria," *Molecular Microbiology*, 9(1):195–209, 1993.

* cited by examiner

FIG. 1

PREPARATION OF ACARIOGENIC SUGAR SUBSTITUTES

This is a Continuation in Part of application Ser. No. 09/168,720, filed Oct. 9, 1998, which is a Divisional Application of U.S. application Ser. No. 08/785,396, now U.S. Pat. No. 5,985,622, filed Jan. 21, 1997, which is a Divisional Application of U.S. application Ser. No. 08/374,155, now U.S. Pat. No. 5,786,140, filed Jan. 18, 1995, which claims priority of DE P 44 01 451.1, filed Jan. 19, 1994 and DE 44 14 185.8, filed Apr. 22, 1994. All of these documents are expressly incorporated by reference. All patents and other publications listed herein are expressly incorporated by reference.

The present invention relates to an improved process for the preparation of non-cariogenic sugars, in particular trehalulose and/or palatinose, using recombinant DNA technology.

The acariogenic sugar substitutes palatinose (isomaltulose) and trehalulose are produced on a large scale from sucrose by an enzymatic rearrangement using immobilized bacterial cells (for example of the species *Protaminobacter rubrum, Erwinia rhapontici, Serratia plymuthica*). This entails the α1→β2 glycosidic linkage existing between the two monosaccharide units of the disaccharide sucrose being isomerized to an α1→6 linkage in palatinose and to an α1→α1 linkage in trehalulose. This rearrangement of sucrose to give the two acariogenic disaccharides takes place with catalysis by the bacterial enzyme sucrose isomerase, also called sucrose mutase. Depending on the organism used, this reaction results in a product mixture which, besides the desired acariogenic disaccharides palatinose and trehalulose, also contains certain proportions of unwanted monosaccharides (glucose and/or fructose). These monosaccharide contents are a considerable industrial problem because elaborate purification procedures (usually fractional crystallizations) are necessary to remove them.

For example EP-0 028 900 describes a method for producing palantinose in a bioreactor by using immobilized sucrose isomerase, which was purified and immobilized from a raw extract by selectively binding to an anionic carrier matrix. The product composition obtained by this method contains, apart from the desired acariogenic disaccharides palantinose and trehalulose, 2.1–2.5% of the unwanted monosaccharide fructose and 0.6–1.0% of the unwanted monosaccharide glucose.

Further, EP-0 483 755 describes a method for producing trehalulose and palatinose, wherein a sucrose solution is contacted with at least one trehalulose-forming enzyme system of a trehalulose-forming microorganism at a temperature of 10–35° C., wherein a mostly tetrahalulose-containing product mixture is obtained, which, however, contains low amounts of the unwanted monosaccharides fructose and glucose. It could further be shown that the amount of unwanted monosaccharides drastically increases by using higher incubation temperatures preferred in large-scale technical methods and, in addition, a rapid thermal inactivation of the enzyme preparations occurred.

One object on which the present invention is based was thus to suppress as far as possible the formation of monosaccharides in the isomerization of sucrose to trehalulose and/or palatinose. Another object on which the present invention is based was to provide organisms which produce palatinose and/or trehalulose in a higher yield than do known organisms.

To achieve these objects, recombinant DNA molecules, organisms transformed with recombinant DNA molecules, recombinant proteins and an improved process for the preparation of non-cariogenic sugars, in particular of palatinose and/or trehalulose, are provided.

The invention relates to a DNA sequence which codes for a protein with a sucrose isomerase activity and comprises
(a) one of the nucleotide sequences shown in SEQ ID NO:1, SEQ ID NO:2, SEQ ID NO:3, SEQ ID NO:9, SEQ ID NO:11 or SEQ ID NO:13, where appropriate without the signal peptide-coding region,
(b) a nucleotide sequence corresponding to the sequences from (a) within the scope of the degeneracy of the genetic code, or
(c) a nucleotide sequence which hybridizes with the sequences from (a) and/or (b).

In the context of the present invention, the term "protein with a sucrose isomerase activity" is intended to embrace those proteins which are able to isomerize sucrose to other disaccharides with conversion of the α1→β2 glycosidic linkage between glucose and fructose in sucrose into another glycosidic linkage between two monosaccharide units, in particular into an α1→6 linkage and/or an α1→α1 linkage. The term "protein with a sucrose isomerase activity" therefore particularly preferably relates to a protein which is able to isomerize sucrose to palatinose and/or trehalulose. Moreover, the proportion of palatinose and trehalulose in the total disaccharides formed by isomerization of sucrose is preferably ≧2%, particularly preferably ≧20% and most preferably ≧50%.

The nucleotide sequence shown in SEQ ID NO:1 codes for the complete sucrose isomerase from the microorganism *Protaminobacter rubrum* (CBS 547.77) including the signal peptide region. The nucleotide sequence shown in SEQ ID NO:2 codes for the N-terminal section of the sucrose isomerase from the microorganism *Erwinia rhapontici* (NCPPB 1578) including the signal peptide region. The nucleotide sequence shown in SEQ ID NO:3 codes for a section of the sucrose isomerase from the microorganism SZ 62 (*Enterobacter* spec.).

The region which codes for the signal peptide in SEQ ID NO:1 extends from nucleotide 1–99. The region coding for the signal peptide in SEQ ID NO:2 extends from nucleotide 1–108. The DNA sequence according to the present invention also embraces the nucleotide sequences shown in SEQ ID NO:1 and SEQ ID NO:2 without the region coding for the signal peptide because the signal peptide is, as a rule, necessary only for correct localization of the mature protein in a particular cell compartment (for example in the periplasmic space between the outer and inner membrane, in the outer membrane or in the inner membrane) or for extracellular export, but not for the enzymatic activity as such. The present invention thus furthermore embraces sequences which also code for the mature protein (without signal peptide) and are operatively linked to heterologous signal sequences, in particular to prokaryotic signal sequences as described, for example, in E. L. Winnacker, Gene und Klone, Eine Einführung in die Gentechnologie, VCH-Verlagsgesellschaft Weinheim, Germany (1985), p. 256.

Nucleotide sequence SEQ ID NO:9 codes for a variant of the isomerase from *Protaminobacter rubrum*. Nucleotide sequence SEQ ID NO:11 codes for the complete isomerase from the isolate SZ 62. Nucleotide sequence SEQ ID NO:13 codes for most of the isomerase from the microorganism MX-45 (FERM 11808 or FERM BP 3619).

Besides the nucleotide sequences shown in SEQ ID NO:1, SEQ ID NO:2, SEQ ID NO:3, SEQ ID NO:9, SEQ ID NO:11 or SEQ ID NO:13, and nucleotide sequences corresponding to one of these sequences within the scope of the degeneracy of the genetic code, the present invention also embraces a DNA sequence which hybridizes with one of these sequences, provided that it codes for a protein which is able to isomerize sucrose. The term "hybridization" according to the present invention is used as in Sambrook et al. (Molecular Cloning. A Laboratory Manual, Cold Spring Harbor Laboratory Press (1989), 1.101–1.104). According to the present invention, hybridization is the word used when a positive hybridization signal is still observed after washing for 1 hour with 1×SSC and 0.1% SDS at 55° C., preferably at 62° C. and particularly preferably at 68° C., in particular for 1 hour in 0.2×SSC and 0.1% SDS at 55° C., preferably at 62° C. and particularly preferably at 68° C. A nucleotide sequence which hybridizes under such washing conditions with one of the nucleotide sequences shown in SEQ ID NO:1 or SEQ ID NO:2, or with a nucleotide sequence which corresponds thereto within the scope of the degeneracy of the genetic code, is a nucleotide sequence according to the invention.

The DNA sequence according to the invention preferably has
  (a) one of the nucleotide sequences shown in SEQ ID NO:1, SEQ ID NO:2, SEQ ID NO:3, SEQ ID NO:9, SEQ ID NO:11 or SEQ ID NO:13, where appropriate without the signal peptide-coding region, or
  (b) a nucleotide sequence which is at least 70% homologous with the sequences from (a).

The DNA sequence according to the invention preferably also has an at least 80% homologous nucleotide sequence to the conserved part-regions of the nucleotide sequences shown in SEQ ID NO:1, SEQ ID NO:2, SEQ ID NO:3, SEQ ID NO:9, SEQ ID NO:11 or SEQ ID NO:13. These conserved part-regions are, in particular, from nucleotide 139–186, nucleotide 256–312, nucleotide 328–360, nucleotide 379–420 and/or nucleotide 424–444 in the nucleotide sequence shown in SEQ ID NO:1.

In a particularly preferred embodiment, the DNA sequence according to the invention has an at least 80% homologous, in particular an at least 90% homologous, nucleotide sequence to the part-regions
  (a) nucleotide 139–155 and/or
  (b) nucleotide 625–644 of the nucleotide sequence shown in SEQ ID NO:1.

Oligonucleotides derived from the above sequence regions have proved suitable as primers for PCR amplification of isomerase fragments from the genomic DNA of a large number of tested microorganisms, for example *Protaminobacter rubrum* (CBS 547.77), *Erwinia rhapontici* (NCPPB 1578), isolate SZ 62 and *Pseudomonas mesoacidophila* MX-45 (FERM 11808).

Particularly preferably used for this purpose are the following oligonucleotides, where appropriate in the form of mixtures, where the bases in parentheses can be present as alternatives:
Oligonucleotide I (17 nt): 5-'TGGTGGAA(A,G)GA(G,A)GCTGT-3'(SEQ ID NO:17)
Oligonucleotide II (20 nt): 5'-TCCCAGTTCAG(G,A)TCCGGCTG-3'(SEQ ID NO:18)

Oligonucleotide I is derived from nucleotides 139–155 of SEQ ID NO:1, and oligonucleotide 11 is derived from the sequence, complementary to nucleotides 625–644, of SEQ ID NO:1. The differences between the homologous part-regions of the DNA sequences according to the invention and the sequences called oligonucleotide I and oligonucleotide II are preferably in each case not more than 2 nucleotides and particularly preferably in each case not more than 1 nucleotide.

In another particularly preferred embodiment of the present invention, the DNA sequence has an at least 80% homologous, in particular an at least 90% homologous, nucleotide sequence to the part-regions of
  (c) nucleotide 995–1013 and/or
  (d) nucleotide 1078–1094
of the nucleotide sequence shown in SEQ ID NO:1.

Oligonucleotides derived from the above sequence regions hybridize with sucrose isomerase genes from the organisms *Protaminobacter rubrum* and *Erwinia rhapontici*. The following oligonucleotides, where appropriate in the form of mixtures, are particularly preferably used, where the bases indicated in parentheses may be present as alternatives:
Oligonucleotide III (19 nt): AAAGATGGCG(G,T)CGAAAAGA (SEQ ID NO: 19)
oligonucleotide IV (17 nt): 5'-TGGAATGCCTT(T,C)TTCTT-3'(SEQ ID NO:20)

Oligonucleotide III is derived from nucleotides 995–1013 of SEQ ID NO:1, and oligonucleotide IV is derived from nucleotides 1078–1094 of SEQ ID NO:1. The differences between the homologous part-regions of the DNA sequences according to the invention and the sequences called oligonucleotide III and IV are preferably in each case not more than 2 nucleotides and particularly preferably in each case not more than 1 nucleotide.

Nucleotide sequences according to the invention can be obtained in particular from microorganisms of the genera *Protaminobacter, Erwinia, Serratia, Leuconostoc, Pseudomonas, Agrobacterium* and *Klebsiella*. Specific examples of such microorganisms are *Protoaminobacter rubrum* (CBS 547.77), *Erwinia rhapontici* (NCPPB 1578), *Serratia plymuthica* (ATCC 15928), *Serratia marcescens* (NCIB 8285), *Leuconostoc mesenteroides* NRRL B-521f (ATCC 10830a), *Pseudomonas mesoacidophila* MX-45 (FERM 11808 or FERM BP 3619), *Agrobacterium radiobacter* MX-232 (FERM 12397 or FERM BP 3620), *Klebsiella* subspecies and *Enterobacter* species. The nucleotide sequences according to the invention can be isolated in a simple manner from the genome of the relevant microorganisms, for example using oligonucleotides from one or more of the conserved regions of SEQ ID NO.1, SEQ ID NO.2, SEQ ID NO. 3, SEQ ID NO. 9, SEQ ID NO.11 and SEQ ID NO.13, by standard techniques of amplification and/or hybridization, and be characterized. The nucleotide sequences according to the invention are preferably obtained by PCR amplification of the genomic DNA of the relevant organism using oligonucleotides I and II. A part-fragment of the relevant sucrose isomerase gene is obtained in this way and can subsequently be used as hybridization probe for isolating the complete gene from a gene bank of the relevant microorganism. Alternatively, the nucleotide sequences can be obtained by producing a gene bank from the particular organism and direct screening of this gene bank with oligonucleotides I, II, III and/or IV.

The present invention further relates to a vector which contains at least one copy of a DNA sequence according to the invention. This vector can be any prokaryotic or eukaryotic vector on which the DNA sequence according to the invention is preferably under the control of an expression signal (promoter, operator, enhancer, etc.). Examples of prokaryotic vectors are chromosomal vectors such as, for example, bacteriophages (for example bacteriophage λ) and extrachromosomal vectors such as, for example, plasmids, with circular plasmid vectors being particularly preferred. Suitable prokaryotic vectors are described, for example, in Sambrook et al., supra, Chapters 1–4.

A particularly preferred example of a vector according to the invention is the plasmid PHWS 88 which harbors a sucrose isomerase gene from *Protaminobacter rubrum* (with the sequence shown in SEQ ID NO:1) under the control of the regulatable tac promoter. The plasmid pHWS 88 was deposited on Dec. 16, 1993, at the Deutsche Sammlung von Mikroorganismen und Zellkulturen (DSM), Mascheroder Weg 1b, 38124 Braunschweig, Germany, under the deposit number DSM 8824 in accordance with the provisions of the Budapest Treaty.

Two further preferred examples of a vector according to the invention are the plasmids pHWG314 and pHWG315, which harbor a sucrose isomerase gene from *Protaminobacter rubrum* and *Pseudomonas mesoacidophila* MX-45, respectively, under the control of a regulatable rhamnose promoter. This promoter is described in Wiese et al. (Arch. Microbiol. 176 (2001):187–196) and Wiese et al. (Appl. Microbiol. 55 (2001), 750–757).

In another preferred embodiment of the present invention, the vector according to the invention is a plasmid which is present in the host cell with a copy number of less than 10, particularly preferably with a copy number of 1 to 2 copies per host cell. Examples of vectors of this type are, on the one hand, chromosomal vectors such as, for example, bacteriophage λ or F plasmids. F plasmids which contain the sucrose isomerase gene can be prepared, for example, by transformation of an *E. coli* strain which contains an F plasmid with a transposon containing the sucrose isomerase gene, and subsequent selection for recombinant cells in which the transposon has integrated into the F plasmid. One example of a recombinant transposon of this type is the plasmid PHWS 118 which contains the transposon Tn 1721 Tet and was prepared by cloning a DNA fragment containing the sucrose isomerase gene from the above-described plasmid pHWS 88 into the transposon pJOE 105 (DSM 8825).

On the other hand, the vector according to the invention can also be a eukaryotic vector, for example a yeast vector (for example YIp, YEp, etc.) or a vector suitable for higher cells (for example a plasmid vector, viral vector, plant vector). Vectors of these types are familiar to the person skilled in the area of molecular biology so that details thereof need not be given here. Reference is made in this connection in particular to Sambrook et al., supra, Chapter 16.

The present invention further relates to a cell which is transformed with a DNA sequence according to the invention or a vector according to the invention. In one embodiment, this cell is a prokaryotic cell, preferably a Gram-negative prokaryotic cell, particularly preferably an enterobacterial cell. It is moreover possible on the one hand to use a cell which contains no sucrose isomerase gene of its own, such as, for example, *E. coli*, but it is also possible, on the other hand, to use cells which already contain such a gene on their chromosome, for example the microorganisms mentioned above as source of sucrose isomerase genes. Preferred examples of suitable prokaryotic cells are *E. coli*, *Protaminobacter rubrum* or *Erwinia rhapontici* cells. The transformation of prokaryotic cells with exogenous nucleic acid sequences is familiar to a person skilled in the area of molecular biology (see, for example, Sambrook et al., supra, Chapter 1–4).

In another embodiment of the present invention, the cell according to the invention may, however, also be a eukaryotic cell such as, for example, a fungal cell (for example yeast), an animal or a plant cell. Methods for the transformation or transfection of eukaryotic cells with exogenous nucleic acid sequences are likewise familiar to the person skilled in the area of molecular biology and need not be explained here in detail (see, for example, Sambrook et al., Chapter 16).

The invention also relates to a protein with a sucrose isomerase activity as defined above, which is encoded by a DNA sequence according to the invention. This protein preferably comprises
  (a) one of the amino-acid sequences shown in SEQ ID NO:4, SEQ ID NO:5, SEQ ID NO:6, SEQ ID NO:10, SEQ ID NO:12 or SEQ ID NO:14, where appropriate without the signal peptide region or
  (b) an amino-acid sequence which is at least 80% homologous with the sequences from (a).

The amino-acid sequence shown in SEQ ID NO:4 comprises the complete sucrose isomerase from *Protaminobacter rubrum*. The signal peptide extends from amino acid 1–33. The mature protein starts at amino acid 34. The amino-acid sequence shown in SEQ ID NO:5 comprises the N-terminal section of the sucrose isomerase from *Erwinia rhapontici*. The signal peptide extends from amino acid 1–36. The mature protein starts at amino acid 37. The amino-acid sequence shown in SEQ ID NO:6 comprises a section of the sucrose isomerase from the microorganism SZ 62. FIG. 1 compares the amino-acid sequences of the isomerases from *P. rubrum*, *E. rhapontici* and SZ 62.

Amino-acid sequence SEQ ID NO:10 comprises a variant of the isomerase from *P. rubrum*. Amino-acid sequence SEQ ID NO:12 comprises the complete isomerase from SZ 62. This enzyme has a high activity at 37° C. and produces only a very small proportion of monosaccharides. Amino-acid sequence SEQ ID NO:14 comprises a large part of the isomerase from MX-45. This enzyme produces about 85% trehalulose and 13% palatinose.

The protein according to the invention particularly preferably has an at least 90% homologous amino-acid sequence to conserved part-regions from the amino-acid sequences shown in SEQ ID NO:4, SEQ ID NO:5, SEQ ID NO:6, SEQ ID NO:10, SEQ ID NO:12 or SEQ ID NO:14, especially in part-regions from
  (a) amino acid 51–149,
  (b) amino acid 168–181,
  (c) amino acid 199–250,
  (d) amino acid 351–387 and/or
  (e) amino acid 390–420
of the amino-acid sequence shown in SEQ ID NO:4.

It is possible by means of the above mentioned DNA sequences, vectors, transformed cells and proteins to provide a sucrose isomerase activity in a simple manner without interfering additional enzymatic activities. Preferably, the sucrose isomerase activity is >30 units/mg and more preferably >45 units/mg. Most preferably the sucrose isomerase activity lies in the range of from 45 units/mg to 150 units/mg.

It is possible for this purpose on the one hand to obtain the sucrose isomerase by recombinant DNA technology as constituent of an extract from the host organism or in isolated and purified form (for example by expression in *E. coli*). This preferably purified and isolated sucrose isomerase enzyme can be used, for example, in immobilized form, for the industrial production of acariogenic sugars such as, for example, trehalulose and/or palatinose by reaction of sucrose in an enzyme reactor. The immobilization of enzymes is familiar to a skilled person and need not be described in detail here.

On the other hand, the production of acariogenic sugars from sucrose can also take place in a complete microorganism, preferably in immobilized form.

Cloning of the abovementioned sucrose isomerase gene into an organism without or with reduced palatinose and/or trehalulose metabolism (that is to say in an organism which is unable significantly to degrade the abovementioned sugars) allows generation of a novel organism which, owing to the introduction of exogenous DNA, is able to produce acariogenic disaccharides with negligible formation of monosaccharides. Thus, suitable for introducing the sucrose isomerase gene is, on the one hand, an organism which is unable to utilize palatinose and/or trehalulose (for example E. coli, bacillus, yeast) and, on the other hand, an organism which would in principle be able to utilize palatinose and/or trehalulose but has reduced palatinose and/or trehalulose metabolism owing to undirected or directed mutation. The term "reduced palatinose and/or trehalulose metabolism" means for the purpose of the present invention that a whole cell of the relevant organism produces, on utilization of sucrose as C source, acariogenic disaccharides but is able to utilize the latter to only a small extent in metabolism, for example by degrading them to monosaccharides. The organism preferably produces less than 2.5%, particularly preferably less than 2%, most preferably less than 1%, of glucose plus fructose based on the total of acariogenic disaccharides and monosaccharide degradation products at a temperature of 15–65° C., in particular of 25–55° C.

The present invention thus further relates to a cell which contains at least one DNA sequence coding for a protein with a sucrose isomerase activity, and has a reduced palatinose and/or trehalulose metabolism as defined above. Preferably the cell according to the invention exhibits such a sucrose isomerase expression rate that the amount of sucrose isomerase expressed in the cell is >10%, preferably >15% and particularly >25% of the total amount of proteins of the cell. A cell of this type produces larger proportions of the non-cariogenic disaccharides trehalulose and/or palatinose and reduced amounts of the interfering byproducts glucose and fructose.

It is possible in one embodiment of the present invention to reduce the palatinose and/or trehalulose metabolism by partial or complete inhibition of the expression of invertase and/or palatinase genes which are responsible for the intracellular degradation of palatinose and/or trehalulose. This inhibition of gene expression can take place, for example, by site-directed mutagenesis and/or deletion of the relevant genes. A site-directed mutation of the palatinase gene shown in SEQ ID NO:7 or of the palatinose hydrolase gene shown in SEQ ID NO:15 can take place, for example, by introduction of a vector which is suitable for homologous chromosomal recombination and which harbors a mutated palatinase gene, and selection for organisms in which such a recombination has taken place.

The principle of selection by genetic recombination is explained in E. L. Winnacker, Gene und Klone, Eine Einf ührung in die Gentechnologie (1985), VCH-Verlagsgesellschaft Weinheim, Germany, pp. 320 et seq.

It is furthermore possible to obtain organisms according to the invention with reduced palatinose and/or trehalulose metabolism by non-specific mutagenesis from suitable starting organisms and selection for palatinase-deficient mutants. One example of a palatinase-deficient mutant of this type is the Protaminobacter rubrum strain SZZ 13 which was deposited on Mar. 29, 1994, at the Deutsche Sammiung von Mikroorganismen und Zellkulturen (DSM), Mascheroder Weg 1b, 38124 Braunschweig, Germany, under deposit number DSM 9121 in accordance with the provisions of the Budapest Treaty. This microorganism was prepared by non-specific mutagenesis of P. rubrum wild-type cells with N-methyl-N'-nitro-N-nitrosoguanidine and is distinguished in that it is no longer able to cleave the non-cariogenic sugars trehalulose and palatinose to glucose and fructose. Selection for such mutants can take place, for example, by using MacConkey palatinose media or minimal salt media with palatinose or glucose as sole C source. The mutants which are white on MacConkey palatinose medium (MacConkey Agar Base from Difco Laboratories, Detroit, Mich., USA (40 g/l) and 20 g/l palatinose) or which grow on minimal salt media with glucose as sole C source but not on corresponding media with palatinose as sole C source are identified as palatinase-deficient mutants.

The present invention furthermore relates to a method for isolating nucleic acid sequences which code for a protein with a sucrose isomerase activity, wherein a gene bank from a donor organism which contains a DNA sequence coding for a protein with a sucrose isomerase activity is set up in a suitable host organism, the clones of the gene bank are examined, and the clones which contain a nucleic acid coding for a protein with sucrose isomerase activity are isolated. The nucleic acids which are isolated in this way and code for sucrose isomerase can in turn be used for introduction into cells as described above in order to provide novel producer organisms of acariogenic sugars.

In this method, the chosen host organism is preferably an organism which has no functional genes of its own for palatinose metabolism, in particular no functional palatinase and/or invertase genes. A preferred host organism is E. coli. To facilitate characterization of palatinose-producing clones it is possible on examination of the clones in the gene bank for sucrose-cleaving clones and the DNA sequences which are contained therein and originate from the donor organism to be isolated and transformed in an E. coli strain which does not utilize galactose and which is used as screening strain for the clones in the gene bank.

On the other hand, the examination of the clones in the gene bank for DNA sequences which code for a protein with a sucrose isomerase activity can also take place using nucleic acid probes derived from the sequences SEQ ID NO:1, SEQ ID NO:2, SEQ ID NO:3, SEQ ID NO:9, SEQ ID NO:11 and SEQ ID NO:13 which code for the sucrose isomerase genes from Protaminobacter rubrum, Erwinia rhapontici and the isolate SZ 62. A DNA fragment obtained by PCR reaction with oligonucleotides I and II as primers, or the oligonucleotides III and/or IV, are particularly preferably used as probes.

The present invention further relates to a process for the production of non-cariogenic sugars, in particular trehalulose and/or palatinose, which comprises using for the production of the sugars (a) a protein with sucrose isomerase activity in isolated form, (b) an organism which is transformed with a DNA sequence which codes for protein with sucrose isomerase activity, or with a vector which contains at least one copy of this DNA sequence, (c) an organism which contains at least one DNA sequence coding for a protein with a sucrose isomerase activity, and has a reduced palatinose and/or trehalulose metabolism, and/or (d) an extract from such a cell or from such an organism.

The process is generally carried out by contacting the protein, the organism or the extract in a suitable medium with sucrose under conditions such that the sucrose is at least partly converted by the sucrose isomerase into acariogenic disaccharides. Subsequently, the acariogenic disaccharides are obtained from the medium or the organism and purified in a known manner.

In a preferred embodiment of this process, the organism, the protein or the extract is used in immobilized form. Proteins (in pure form or in extracts) are preferably immobilized by coupling of reactive side groups (for example NH$_2$ groups) to a suitable carrier. Immobilization of cells takes place, for example, in a sodium alginate/calcium chloride solution. A review of suitable methods for immobilizing cells and proteins is given, for example, in I. Chibata (Immobilized Enzymes, John Wiley and Sons, New York, London, 1978).

It is possible on use of a cell transformed with the sucrose isomerase gene to increase the rate of production of acariogenic sugars by comparison with known organisms by increasing the number of gene copies in the cell and/or by increasing the expression rate in a combination with strong promoters. It is furthermore possible by transformation of a cell which is unable or able to only a limited extent to utilize acariogenic sugars with the sucrose isomerase gene to produce a transformed cell with whose aid it is possible to obtain acariogenic sugars, in particular palatinose and/or trehalulose, without or with fewer byproducts.

On use of a microorganism with reduced palatinose and/or trehalulose metabolism, which already contains a functional sucrose isomerase gene, transformation with an exogenous sucrose isomerase gene is not essential but may be carried out to improve the yields.

Finally, the present invention also relates to a DNA sequence which codes for a protein with palatinase or palatinose hydrolase activity and comprises (a) one of the nucleotide sequences shown in SEQ ID NO:7 or SEQ ID NO:15, (b) a nucleotide sequence which corresponds to the sequence from (a) within the scope of the degeneracy of the genetic code or (c) a nucleotide sequence which hybridizes with the sequences from (a) and/or (b).

The invention further relates to a vector which contains at least one copy of the above mentioned DNA sequence and to a cell which is transformed with a DNA sequence or a vector as mentioned above. The invention likewise embraces a protein with palatinase activity which is encoded by a DNA sequence as indicated above and which preferably has one of the amino-acid sequences shown in SEQ ID NO:8 or SEQ ID NO:16.

The palatinase from *P. rubrum* shown in SEQ ID NO:8 differs from known sucrose-cleaving enzymes in that it cleaves the sucrose isomers which are not cleaved by known enzymes, in particular palatinose.

The amino acid sequence shown in SEQ ID NO:16 comprises a palatinose hydrolase from MX-45, which cleaves palatinose to form fructose and glucose. The gene-coding for this enzyme is shown in SEQ ID NO:15 and is located in the genome of MX-45 on the 5' side of the isomerase gene shown in SEQ ID NO:13.

The invention is further described by the following sequence listings and figures:

SEQ ID NO:1 shows the nucleotide sequence of the gene coding for the sucrose isomerase from *Protaminobacter rubrum*. The sequence coding for the signal peptide terminates at nucleotide No. 99.

SEQ ID NO:2 shows the N-terminal section of the nucleotide sequence of the gene coding for the sucrose isomerase of *Erwinia rhapontici*. The sequence coding for the signal peptide terminates at the nucleotide with No.108.

SEQ ID NO:3 shows a section of the nucleotide sequence of the gene coding for the sucrose isomerase from the isolate SZ 62.

SEQ ID NO:4 shows the amino-acid sequence of the sucrose isomerase from *Protaminobacter rubrum*.

SEQ ID NO:5 shows the N-terminal section of the amino-acid sequence of the sucrose isomerase from *Erwinia rhapontici*.

SEQ ID NO:6 shows a section of the amino-acid sequence of the sucrose isomerase from the isolate SZ 62.

SEQ ID NO:7 shows the nucleotide sequence for the palatinase gene from *Protaminobacter rubrum*.

SEQ ID NO:8 shows the amino-acid sequence of the palatinase from *Protaminobacter rubrum*.

SEQ ID NO:9 shows the nucleotide sequence of a variant of the sucrose isomerase gene from *P. rubrum*.

SEQ ID NO:10 shows the corresponding amino-acid sequence.

SEQ ID NO:11 shows the complete nucleotide sequence of the sucrose isomerase gene from SZ 62.

SEQ ID NO:12 shows the corresponding amino-acid sequence.

SEQ ID NO:13 shows most of the sucrose isomerase gene from *Pseudomonas mesoacidophila* (MX-45).

SEQ ID NO:14 shows the corresponding amino acid sequence.

SEQ ID NO:15 shows the palatinose hydrolase gene from *Pseudomonas mesoacidophila* (MX-45).

SEQ ID NO:16 shows the corresponding amino-acid sequence.

FIG. 1 shows a comparison of the amino-acid sequences of the sucrose isomerases from *Protaminobacter rubrum* (to the 208$^{th}$ amino acid of SEQ ID NO:4), *Erwinia rhapontici* (to the 208$^{th}$ amino acid of SEQ ID NO:5) and the isolate SZ 62 (SEQ ID NO:6), FIG. 2 shows the cloning diagram for the preparation of the recombinant plasmid pHWS 118 which contains the sucrose isomerase gene on the transposon Tn 1721, FIG. 3 shows the diagram for the preparation of *E. coli* transconjugants which contain the sucrose isomerase gene of a F plasmid and FIG. 4 shows a comparison between the saccharides produced by *P. rubrum* wild-type cells and cells of the *P. rubrum* mutant SZZ 13.

Figure 2:
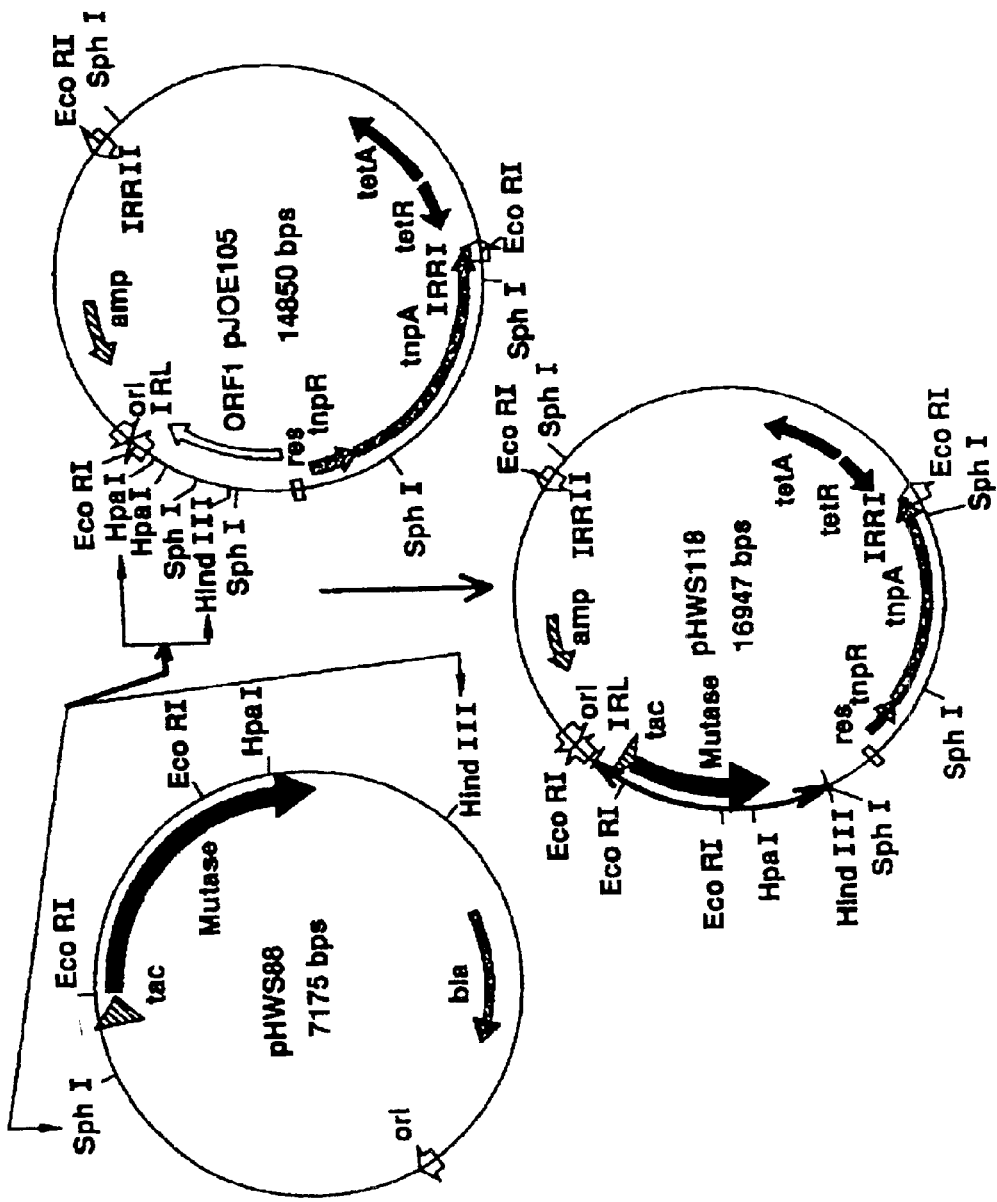

The following examples serve to illustrate the present invention.

EXAMPLE 1

Isolation of the Sucrose Isomerase Gene from *Protaminobacter rubrum*

Complete DNA from the organism *Protaminobacter rubrum* (CBS 574.77) was partially digested with Sau3A I. Collections of fragments with a size of about 10 kBp were obtained from the resulting fragment mixture by elution after fractionation by gel electrophoresis and were ligated into a derivative, which had been opened with BamHI, of the lambda EMBL4 vector derivative λ RESII (J. Altenbuchner, Gene 123 (1993), 63–68). A gene bank was produced by transfection of *E. coli* and transformation of the phages into plasmids according to the above reference. Screening of the kanamycin-resistant colonies in this gene bank was carried out with the radiolabeled oligonucleotide S214 which was derived from the sequence of the N terminus of the mature isomerase by hybridization:

```
S214:  5'-ATCCCGAAGTGGTGGAAGGAGGC-3'  (SEQ ID NO:21)
          T A A        A A
```

Subsequently, the plasmid DNA was isolated from the colonies with a positive reaction after appropriate cultivation. After a restriction map had been drawn up, suitable subfragments were sequenced from a plasmid pKAT 01 obtained in this way, and thus the complete nucleotide sequence, which is shown in SEQ ID NO:1, of the DNA coding for isomerase was obtained. The amino-acid sequence derived therefrom corresponds completely to the peptide sequence of the mature isomerase obtained by sequencing (Edmann degradation). A cleavage site for SacI is located in the non-coding 3' region of this isomerase gene, and a cleavage site for HindIII is located in the non-coding 5' region. This makes it possible to subclone the intact isomerase gene into the vector pUCBM 21 (derivative of the vector pUC 12, Boehringer Mannheim GmbH, Mannheim, Germany) which had previously been cleaved with the said enzymes. The resulting plasmid was called pHWS 34.2 and confers on the E. coli cells harboring it the ability to synthesize sucrose isomerase.

A variant of the sucrose isomerase gene from P. rubrum has the nucleotide sequence shown in SEQ ID NO:9.

EXAMPLE 2

Cloning and Expression of the Sucrose Isomerase from P. rubrum in E. coli

1. Preparation of the Plasmid pHWS88

The non-coding 5' region of the sucrose isomerase gene was deleted from the plasmid pHWS 34.2, using an oligonucleotide S434 with the sequence 5'-CGGAATTCTTATGCCCCGTCAAGGA-3'(SEQ ID NO:22), with simultaneous introduction of an EcoRI cleavage site (GAATTC). The isomerase gene derivative obtained in this way was treated with BstE II, the protruding BstE II end was digested off with S1 nuclease and subsequently digestion with EcoRI was carried out. The isomerase gene treated in this way was cloned into the vector pBTacI (Boehringer Mannheim GmbH, Mannheim, Germany) which had been pretreated with EcoRI and SmaI. The resulting vector PHWS 88 (DSM 8824) contains the modified isomerase gene with a preceding EcoRI restriction site in front of the ATG start codon, and the 3' region of the isomerase gene up to the S1-truncated BstE II cleavage site. On induction with IPTG, this vector confers on the cells harboring this plasmid the ability to produce isomerase and resistance to ampicillin (50 to 100 μg/ml). Preferably used for producing isomerase are E. coli host cells which overproduce the lac repressor.

2. Preparation of the Plasmid pHWS118::Tn1721Tet

The gene cassette for the sucrose mutase was incorporated into a transposon.

This took place by cloning an SphI/HindIII DNA fragment from the plasmid pHWS88, which harbors the sucrose mutase gene under the control of the tac promoter, into the plasmid pJOE 105 on which the transposon Tn 1721 is located. The plasmid pJOE105 was deposited on Dec. 16, 1993, at the DSM under the deposit number DSM 8825 in accordance with the provisions of the Budapest Treaty. The resulting plasmid pHWS118, on which the sucrose mutase gene is under the control of the regulatable tac promoter, was used to transform a E. coli strain containing an F' plasmid. FIG. 2 shows the cloning diagram for the preparation of pHWS 118 from pHWS88 and pJOE 105.

Figure 3:
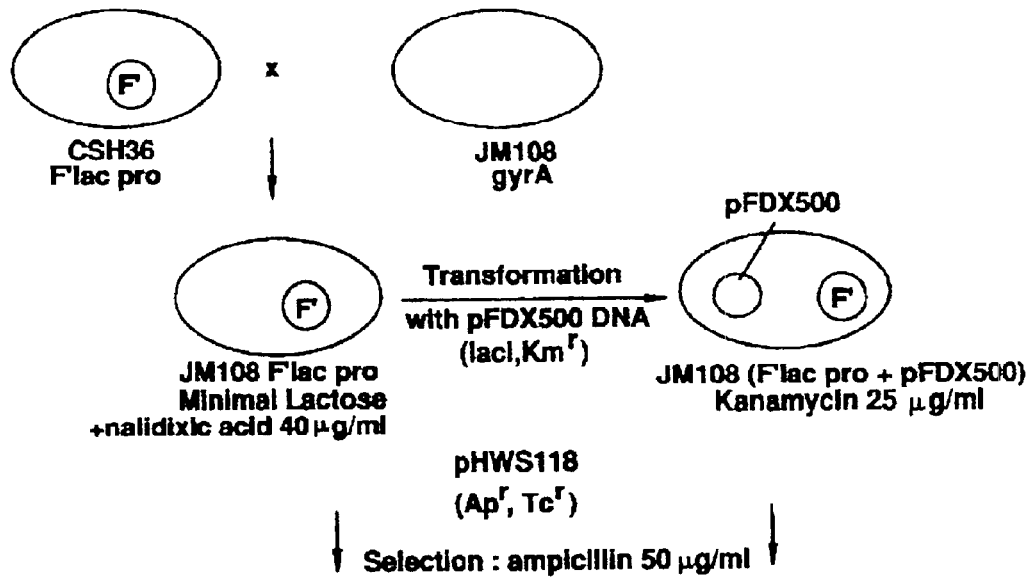
Figure 3:
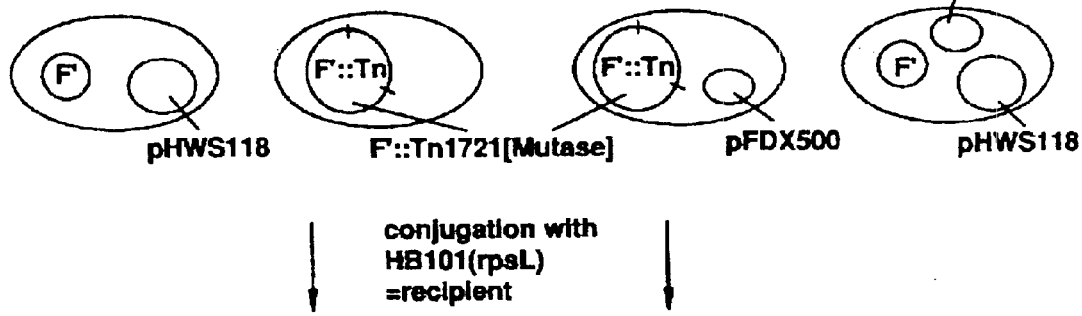
Figure 3:
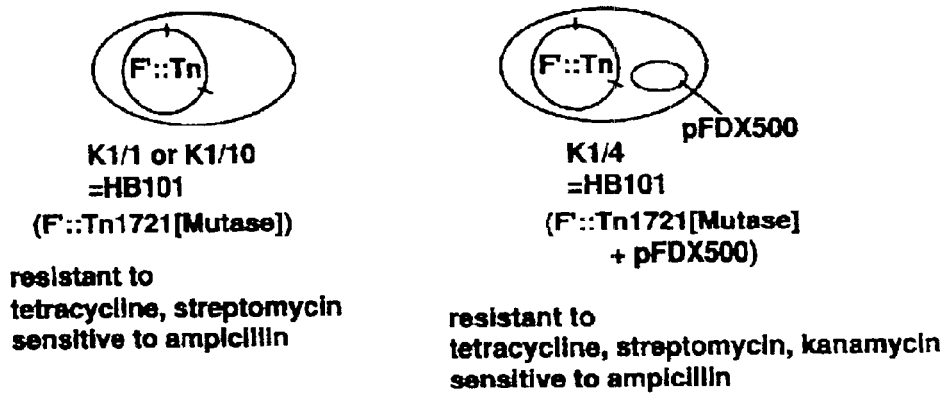

E. coli transconjugants containing the sucrose mutase gene were prepared as described in the diagram in FIG. 3. For this purpose, firstly the F'-harboring E. coli strain CSH36 (J. H. Miller, Experiments in Molecular Genetics, Cold Spring Harbor Laboratory (1972), p. 18), which carries the Lac+ phenotype mediated by the F' plasmid, was crossed with the E. coli strain JM108 which is resistant to nalidixic acid (Sambrook et al., supra, p. A9–A13). Selection on minimal medium to which lactose, proline and nalidixic acid were added resulted in an F'-Lac-harboring transconjugant. This was additionally transformed with the Iq plasmid FDX500 (Brinkmann et al., Gene 85 (1989), 109–114) in order to permit control of the sucrose mutase gene by the tac promoter.

The transconjugant prepared in this way was transformed with the transposon plasmid pHWS118 harboring the sucrose mutase gene. For selection of transconjugants, crossing into the streptomycin-resistant E. coli strain HB101 (Boyer and Roulland-Dussoix, J. Mol. Biol 41 (1969), 459–472) was carried out. Transfer of the tetracycline resistance mediated by the transposon was possible only after transposition of the modified Tn1721Tet from the plasmid pHWS118, which is not capable of conjugation or mobilization, to the F' plasmid which is capable of conjugation. Transmission of the F' plasmid with the modified transposon in HB101 was selected on LB plates containing streptomycin and tetracycline, and retested on ampicillin and nalidixic acid plates.

3. Expression of the Sucrose Isomerase in E. coli

Examination of the enzyme production by such F' plasmid-harboring E. coli cells showed that it was possible to produce sucrose mutase protein. F' plasmid-containing HB101 cells which harbored no additional Lac repressor plasmid (for example K1/1 or K1/10) produced sucrose mutase protein in identical amounts with and without the inducer isopropyl β-D-thiogalactoside (IPTG). The productivities of three transconjugants K1/1, K1/10 and K1/4 are shown in Table 1.

It was possible to observe normal growth of the E. coli cells during production of sucrose mutase protein.

Introduction of the sucrose mutase gene into the F□ plasmid in the presence of the repressor-encoded plasmid pFDX500 (see transconjugants K1/4) made it possible to control enzyme production with the inducer IPTG. Whereas no enzymatic activity was measured without IPTG, production of about 1.6 U/mg sucrose mutase protein was obtainable after induction for 4 hours.

No adverse effect on cell growth was observable. The plasmid-harboring E. coli cells reached a density of about 3 $OD_{600}$ after induction for 4 hours.

Up to 1.6 U/mg sucrose mutase activity were measured in transformed E. coli. The synthetic performance is comparable to that of P. rubrum. Analysis of the produced enzyme by SDS gel electrophoresis provides no evidence of inactive protein aggregates. The band of the sucrose mutase protein was only weakly visible with Coomassie staining and was detectable clearly only in a Western blot. It was possible to correlate the strength of the protein band and the measured enzymatic activity in the production of sucrose mutase in E. coli.

EXAMPLE 3

Isolation of the Sucrose Isomerase Gene from *Erwinia rhapontici*

A gene bank was produced by restriction cleavage of the complete DNA from *Erwinia rhapontici* (NCPPB 1578) in the same way as described in Example 1.

Using the primer mixtures

```
5'-TGGTGGAAAGAAGCTGT-3' (SEQ ID NO:23) and
        G  G

5'-TCCCAGTTCAGGTCCGGCTG-3' (SEQ ID NO:24),
        A
```

PCR amplification resulted in a DNA fragment with whose aid it is possible to identify colonies containing the mutase gene by hybridization.

In this way, a positive clone pSST2023 which contains a fragment, 1305 nucleotides long, of the *Erwinia* isomerase gene was found. The nucleotide sequence of this fragment is depicted in SEQ ID NO:2.

Sequence comparison with the *Protaminobacter* gene reveals an identity of 77.7% and a similarity of 78% for the complete gene section including the signal peptide region, and an identity of 83.4% and a similarity of 90.3% at the amino-acid level.

Figure 1:
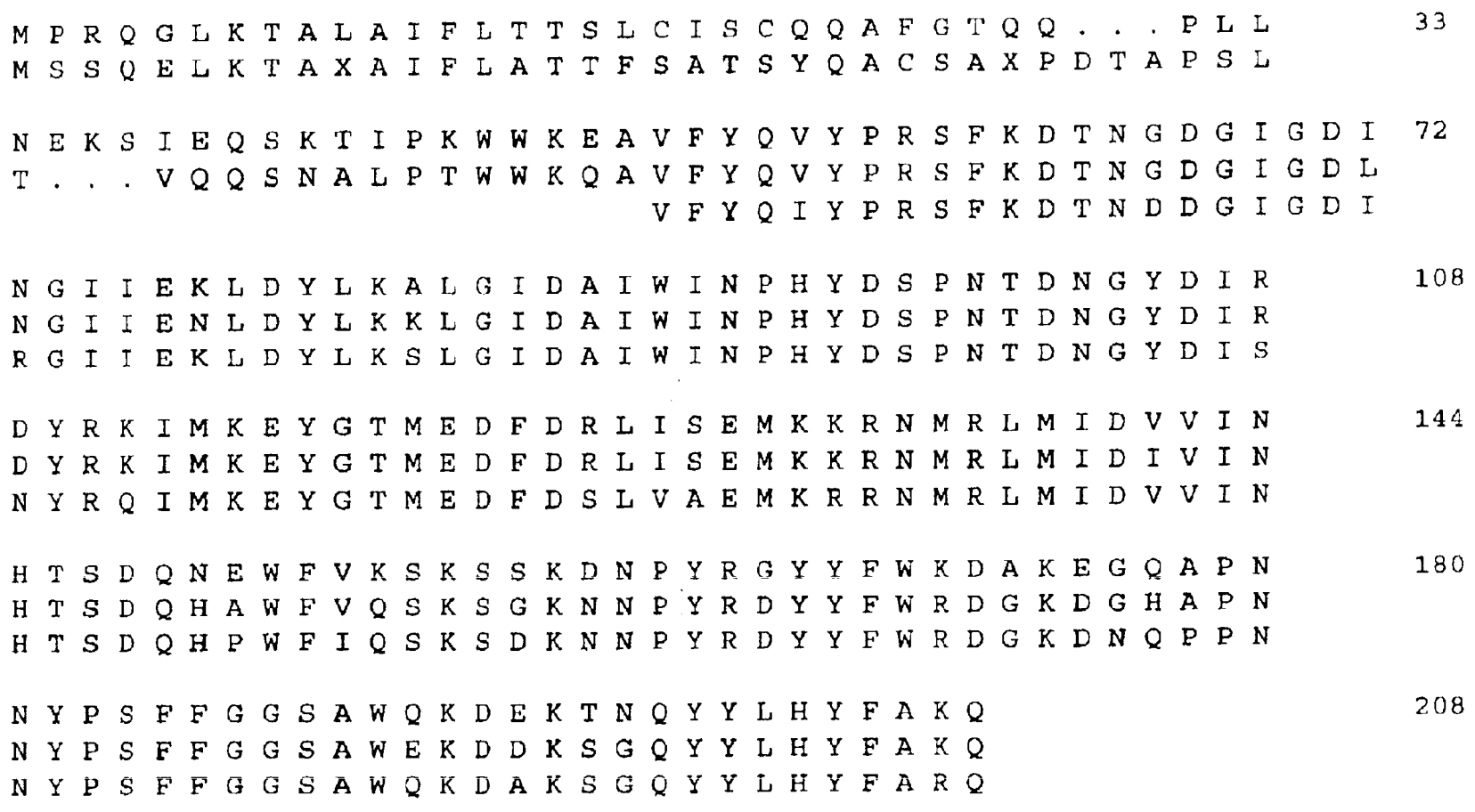

The sequence differences are mainly concentrated in the signal peptide region. For this reason, only the enzyme-encoding region responsible for the actual mutase activity, without the signal peptide, should be considered for comparison. From these viewpoints, the identity or similarity at the nucleotide level emerges as 79%. Comparison of the amino-acid sequences (FIG. 1) in this section shows 87.9% identical amino acids. Of 398 amino acids (this corresponds to 71% of the complete enzyme) in the *Erwinia* mutase, 349 are the same as in *Protaminobacter*. 25 of 48 exchanged amino acids show strong similarity so that the overall similarity at the AA level emerges as 94%. The AA exchanges are mainly concentrated in the region between amino acid 141 and 198. In front of this region there is a sequence of 56 conserved amino acids. Other sections also exhibit particularly high conservation (see FIG. 1).

These data show that, for the section cloned and sequenced to date, overall there is very extensive conservation of the two mutases from *Erwinia* and *Protaminobacter*.

Identity of the Cloned Mutase Gene from *Erwinia*

The probe chosen for a rehybridization experiment with genomic *Erwinia* DNA was the SspI/EcoRI fragment, which is about 500 bp in size, from pSST2023. This fragment was used, after digoxigenin labeling, for hybridization with *Erwinia* DNA with high stringency (68° C.). Complete *Erwinia* DNA cut with SspI/EcoRI showed a clear hybridization signal with the expected size of about 500 bp. *Erwinia* DNA cut only with SspI showed a hybridization signal of about 2 kb.

It was possible to verify by the successful rehybridization of pSST2023 with genomic *Erwinia* DNA that the mutase region cloned into pSST2023 originates from *Erwinia rhapontici*.

Cloning of the C-terminal Part-fragment of the *Erwinia* Mutase

The N-terminal part-fragment of the *Erwinia* mutase gene which has been cloned to date has a size of 1.3 kb and has the nucleotide sequence shown in SEQ ID NO:2. Since it can be assumed that the complete *Erwinia* gene is virtually identical in size to the known *Protaminobacter* gene (1.8 kb), a section of about 500 bp is missing from the C-terminal region of the *Erwinia* gene.

The SspI fragment which is about 2 kb in size from the complete *Erwinia* DNA was selected for cloning of the *Erwinia* C-terminus. In a Southern blot, this fragment provides a clear signal with a digoxigenin-labeled DNA probe from pSST2023. This 2 kb SspI fragment overlaps by about 500 bp at the 3' end with the region already cloned in pSST2023. Its size ought to be sufficient for complete cloning of the missing gene section of about 500 bp. The digoxigenin-labeled fragment probe SspI/EcoRI from pSST2023 is suitable for identifying clones which are sought.

EXAMPLE 4

Preparation of a *Protaminobacter* Palatinase-deficient Mutant

Figure 4B:
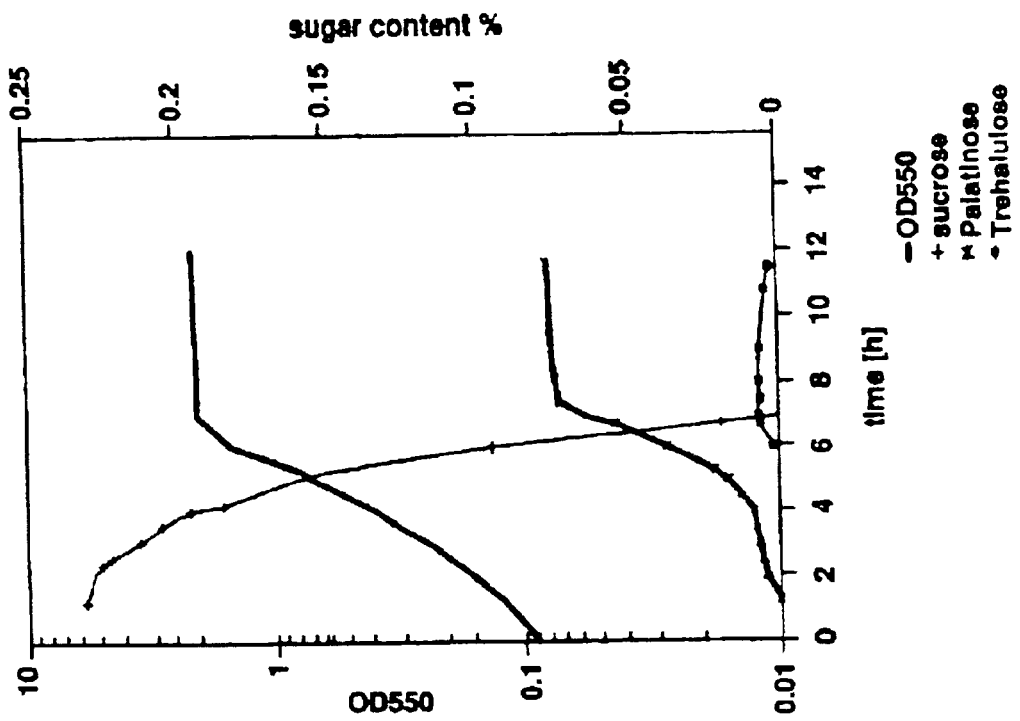
Figure 4A:
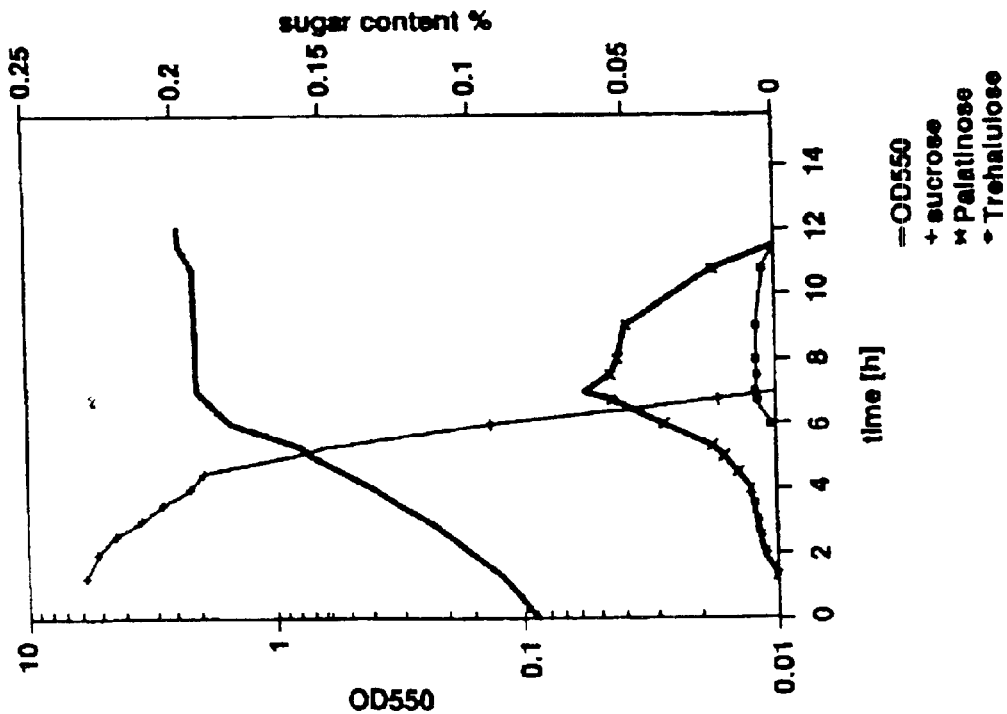

Cells of *Protoaminobacter rubrum* (CBS 547, 77) were mutagenized with N-methyl-N'-nitro-N-nitroso-guanidine by the method of Adelberg et al. (Biochem. Biophys. Research Commun. 18 (1965), 788) as modified by Miller, J., (Experiments in Molecular Genetics, Cold Spring Harbor Laboratory, 125–179 (1972)). Palatinase-deficient mutants were selected using MacConkey palatinose medium (MacConkey Agar Base (Difco Laboratories, Detroit, Mich., USA), 40 g/l with the addition of 20 g/l palatinose, sterilized by filtration, 25 mg/l kanamycin) and minimal salt media (10.5 g of $K_2HPO_4$, 4.5 g of $KH_2PO_4$, 1 g of $(NH_4)_2SO_4$, 0.5 g of sodium citrate $2H_2O$, 0.1 g of $MgSO_4$ $7H_2O$), 1 mg of thiamine, 2 g of palatinose or glucose, 25 mg of kanamycin and 15 g of agar per liter, pH 7.2). Mutants of *P. rubrum* which are white on MacConkey palatinose medium or grow on minimal salt medium with glucose in contrast to the same medium with palatinose are identified as palatinase-deficient mutants. The enzyme activity of cleaving palatinose to glucose and fructose (palatinase activity) cannot, in contrast to the wild-type, be detected in cell extracts from these mutants. On cultivation of these cells in minimal salt medium with 0.2% sucrose as sole C source there is, in contrast to the wild-type cells in which palatinose can be detected only transiently in the time from 4 to 11 hours after starting the culture, a detectable continuous accumulation of palatinose (isomaltulose). Overnight cultures in the same medium contain no palatinose in the case of the wild-type cells but contain >0.08% palatinose in the case of the mutant SZZ 13 (DSM 9121) prepared in this way (see FIG. 4).

EXAMPLE 5

Immobilization of Microorganism Cells

Cells are rinsed off a subculture of the appropriate strain using 10 ml of a sterile nutrient substrate composed of 8 kg of concentrated juice from a sugar factory (dry matter content=65%), 2 kg of corn steep liquor, 0.1 kg of $(NH_4)_2HPO_4$ and 89.9 kg of distilled water, pH 7.2. This suspension is used as inoculum for preculture in 1 l flasks containing 200 ml of nutrient solution of the above composition in shaking machines. After an incubation time of 30 hours at 29° C., 10 flasks (total contents 2 l) are used to inoculate 18 l of nutrient solution of the above composition in a 30 l small fermenter, and fermentation is carried out at 29° C. and a stirring speed of 350 rpm introducing 20 l of air per minute.

After organism counts above $5 \times 10^9$ organisms per ml are reached, the fermentation is stopped and the cells are harvested from the fermenter solution by centrifugation. The cells are then suspended in a 2% strength sodium alginate solution and immobilized by dropwise addition of the suspension to a 2% strength calcium chloride solution. The resulting immobilizate beads are washed with water and can be stored at +4° C. for several weeks.

Cells of the palatinase-deficient mutant SZZ 13 (DSM 9121) show better catalytic properties in respect of their product composition than do comparable cells from the known microorganisms *Protaminobacter rubrum* (CBS 547.77) and *Erwinia rhapontici* (NCPPB 1578).

Whole cells and crude extracts of SZZ 13, and an immobilizate of SZZ 13 in calcium alginate prepared as above, were evaluated in respect of product composition in an activity assay. Before the actual activity assay, the immobilizate was swollen in 0.1 mol/l potassium phosphate buffer, pH 6.5.

The activity measurements at 25° C. revealed that no fructose and glucose were found with the mutant SZZ 13, while with *P. rubrum* wild-type cells 2.6% fructose and glucose (based on the total of mono- and disaccharides) were found in whole cells and 12.0% were found in the crude extract. In the case of *E. rhapontici*, 4% glucose and fructose were found in whole cells, and 41% in the crude extract.

EXAMPLE 6

Isolation of the Sucrose Isomerase Gene from other Microorganisms

Partial digestion of genomic DNA from the isolate SZ62 (*Enterobacter* spec.), the organism *Pseudomonas mesoacidophila* (MX-45) or from another microorganism and insertion of the resulting fragments into suitable *E. coli* vectors and transformation result in a gene bank whose clones contain genomic sections between 2 and 15 kb of the donor organism.

Those *E. coli* cells which harbor these plasmids and which display a red coloration of the colony are selected by plating on McConkey palatinose medium. The plasmid DNA contained in these cells is transferred into an *E. coli* mutant which is unable to grow on galactose as sole C source (for example ED 8654, Sambrook et al., supra, pages A9–A13).

This transformed cell line is able to identify palatinose producers in the gene bank which has been prepared as described above from DNA of the donor organism.

To identify the palatinose-producing clones which are sought, the cells of the gene bank are isolated and cultured on minimal salt media containing galactose and sucrose. After replica plating of the colonies on plates containing the same medium, the cells are killed by exposure to toluene vapor. Subsequently, cells of the screening strain are spread as lawn in minimal salt soft agar without added C source over the colonies of the gene bank and incubated. Significant growth of the cells of the screening strain appears only at the location of cells in the gene bank which have produced palatinose. The isomerase content emerges on testing the cells of the replica control.

These *E. coli* clones identified in this way are unable to grow on palatinose as sole C source in the medium, show no ability to cleave sucrose in a test on whole cells or on cell extracts, but on cultivation under these conditions and without addition of sucrose to the medium produce palatinose.

Alternatively, isomerase clones can also be identified using a PCR fragment prepared by the procedure of Example 3.

Use of plasmid DNA from the *E. coli* clones identified in this way as probes for hybridization on filters with immobilized DNA from the donor organism allows the gene regions which harbor isomerase genes to be detected and specifically made available.

A clone which contains the nucleotide sequence shown in SEQ ID NO:3, with the amino-acid sequence which, is derived therefrom and shown in SEQ ID NO:6, was identified in this way. In the same way an isomerase clone from DNA of the bacterial strain *Pseudomonas mesoacidophila* MX-45 (FERM 11808) was found.

The complete nucleotide sequence and amino-acid sequence of the sucrose isomerase from SZ 62 are depicted in SEQ ID NO:11 and 12. A large part of the nucleotide sequence and amino-acid sequence of the sucrose isomerase from MX-45 are depicted in SEQ ID NO:13 and 14.

EXAMPLE 7

Cloning of a Palatinase Gene

The *Protaminobacter rubrum* gene bank prepared in Example 1 was screened with the radiolabeled oligonucleotide mixture S433 which was derived from the sequence of the N-terminus of the isolated palatinase and had the sequence CA(G,A)TT(C,T)GG(T,C)TA(C,T)GG-3'(SEQ ID NO:25).

A positive clone was found, and a plasmid named pKAT 203 was isolated therefrom.

*E. coli* cells which harbor the plasmid pKAT 203 are able to metabolize palatinose. The cleavage of palatinose to glucose and fructose which is detectable in the activity assay suggests that there is a "palatinase".

It is possible by sequencing pKAT203 DNA with the oligonucleotide S433 as primer to obtain a DNA sequence from which it was possible to read off, after translation into amino-acid sequence data, the N-terminal amino acids known to us. An open reading frame was obtained by a subsequent sequencing step.

Determination of the Sequence of the "Palatinase" Gene

For further sequencing of the "palatinase" gene, part-fragments from the plasmid pKAT 203 were selected on the basis of the restriction map and subcloned in the M13 phage system, and a sequencing of the single-stranded phage DNA was carried out with the universal primer 5'-GTTTTCCCAGTCACGAC-3'(SEQ ID NO:26).

Combination of the resulting DNA sequence data for the individual fragments taking account of overlapping regions allows a continuous reading frame of 1360 base pairs to be determined for the "palatinase" (SEQ ID NO:7).

Translation of this DNA sequence into amino-acid data reveals a protein with 453 amino acids (SEQ ID NO:8) and a molecular weight, which can be deduced therefrom, of about 50,000 Da. This is consistent with the finding that a protein fraction which had a band at about 48,000 Da in the SDS gel was obtainable by concentration of the "palatinase" activity. In the native gel, the palatinose-cleaving activity was attributable to a band with a size of about 150,000 Da.

Comparisons of Homology with Other Known Proteins

Comparison of the amino-acid sequence derivable from the DNA sequence with data stored in a gene bank (SwissProt) revealed a homology with melibiase from *E. coli* (MeIA) (in two parts: identity 32%).

EXAMPLE 8

Cloning of a Palatinose Hydrolase Gene from *P. mesoacidophila* MX-45.

A gene with the nucleotide sequence shown in SEQ ID NO:15 was isolated from the gene bank prepared from the microorganism *P. mesoacidophila* MX-45 in Example 6. This gene codes for a protein with the amino-acid sequence shown in SEQ ID NO:16. The protein is a palatinose hydrolase which catalyzes the cleavage of palatinose to form fructose and glucose.

EXAMPLE 9

Cloning and Expression of the Sucrose Isomerase from *Protaminobacter Rubrum* and *Pseudomonas Mesoacidophila* MX-45 in *E. coli*

1. Preparation of the Plasmids pHWG314 and pHWG315

Figure 5:
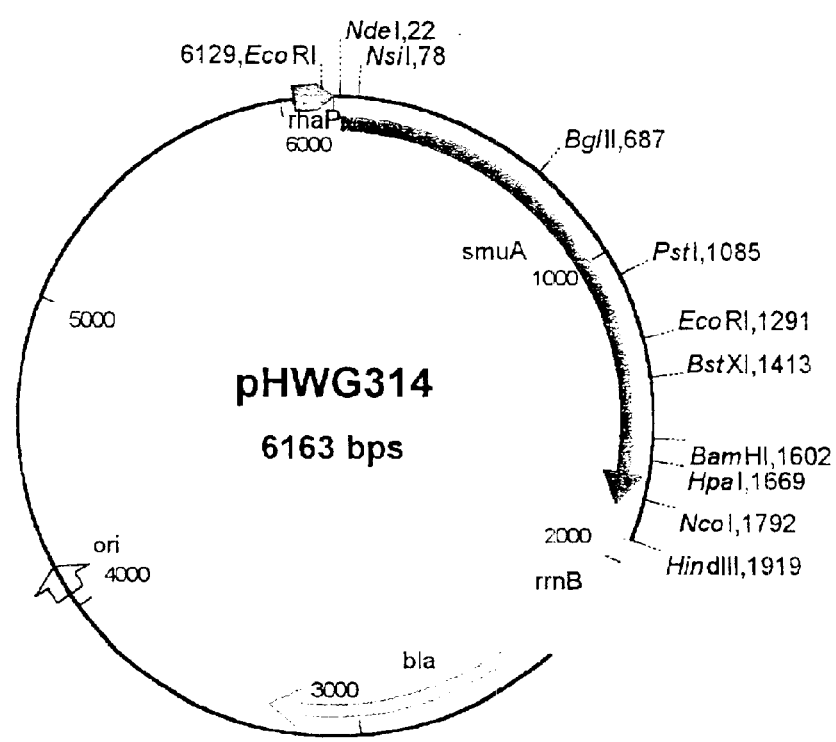
FIG. 5 shows plasmid pHWG314.
Figure 6:
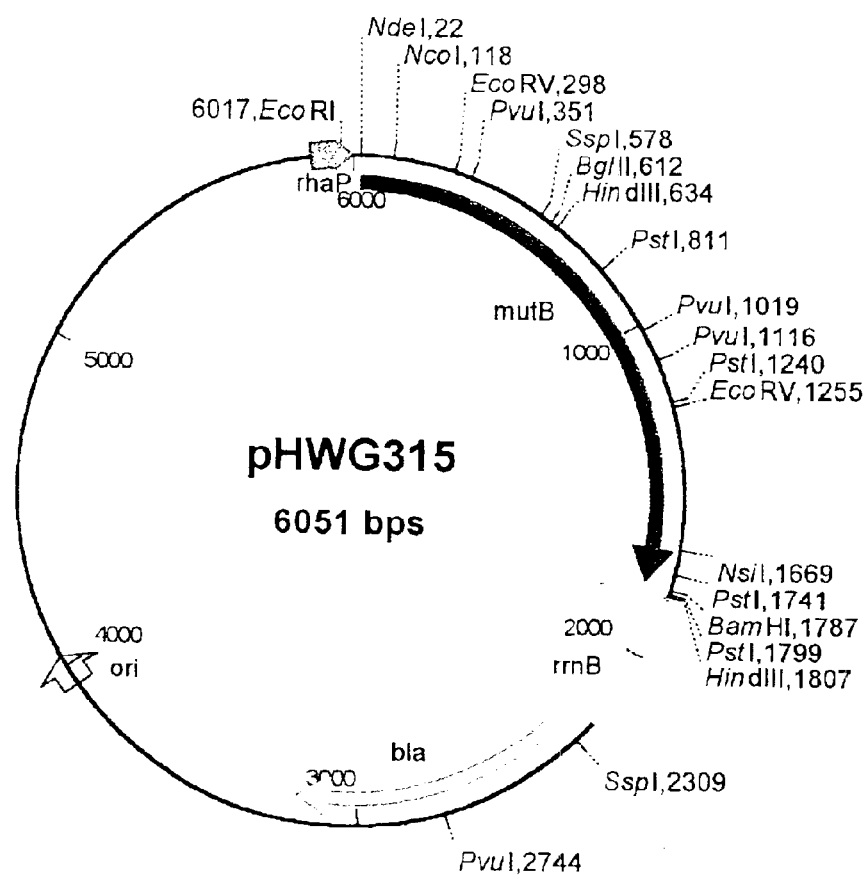
FIG. 6 shows plasmid pHWG315.

The plasmids were prepared by inserting the gene modules into the vector pJOE2702 (Wiese et al. (2001) supra) digested with NdeI/HindIII (314) and NdeI/BamHI (315), respectively. The plasmids carry the entire sequence coding for each mutase. FIGS. 5 and 6 show the restriction maps of both plasmids. *E. coli* JM109 was used as host.

2. Expression of the Sucrose Isomerase in *E.coli* and Isolation

The production of the enzyme was induced by adding 0.2% rhamnose to the medium. The cells were harvested via centrifugation and sonification. Standard conditions were applied, as described in the other examples. For the purification from *E. coli* a chromatography of the raw extract was performed using a cation exchange chromatography column, e.g. a MonoS column (Pharmacia). The material was loaded on the column in the presence of 10 mM Ca-acetate, pH 6.5. The elution was carried out with a NaCl gradient of from 0–100 mM. Then the fractions were tested for their protein content. All results are contained in Table 2.

3. Isolation of the Sucrose Isomerase from *Protaminobacter rubrum* and *Pseudomonas mesoacidophila* MX45

The enzymes from the (wild-type) strains *Protaminobacter rubrum* and *Pseudomonas mesoacidophila* were not purified. Purification according to the above protocol was successful only regarding the enzymes produced in *E. coli*.

After cultivation in a suitable complete medium containing 2% sucrose the cells of the wild-type strains were harvested at 30° C. and decomposed. Then the enzymatic activity and the protein content were determined.

Surprisingly, the recombinant sucrose isomerase can be separated by a one-step procedure from homologous proteins in the *E. coli* extract exhibiting high yield and purity. Apparently the recombinant protein has a different charge composition compared to the isomerase from native organisms.

A comparison of the results shown in Table 2 shows that with the help of the recombinant *E.coli* strains significantly higher sucrose isomerase yields can be obtained than with the wild-type strains *Pseudomonas mesoacidophila* MX-45 and *Protominobacter rubrum*. The amount of recombinant sucrose isomerase expressed in the *E. coli* strains is about 15.6 and 28.9%, respectively, of the total amount of proteins in the cell. Contrary thereto, the amount of sucrose isomerase formed in the wild-type strains *Pseudomonas mesoacidophila* MX-45 and *Protominobacter rubrum* was so small that it could not be detected by using conventional detection methods. Furthermore, the activity of the recombinant sucrose isomerase is about 10-times higher than the activity of the sucrose isomerase formed in the respective wild-type strains. Consequently, the protein isolated from the wild-type strains must have been inactivated to a great extent when isolated from the wild-type strains.

TABLE 1

Surose mutase activity in *E. coli* HB101 (F'::Tn1721 [Mutase])

| Strain | U/mg mutase after 4 hours without induction | U/mg mutase after 4 hours induction with 50 µM IPTG |
|---|---|---|
| K1/1 | 1.0 | 1.2 |
| K1/10 | 0.9 | 1.1 |
| K1/4 | 0 | 1.6 |

TABLE 2

The results obtained under items 3 and 4 of example 9 are summarized in the following table:

| Expression in *E. coli* (plasmid) | Wild-type strain | Gene | Culture Vol. (ml) | OD$_{600}$ | U ml$^{-1}$ | mg ml$^{-1}$ | U in mg ml$^{-1}$ | U (total) | pure U in mg$^{-1}$ | % cell protein |
|---|---|---|---|---|---|---|---|---|---|---|
| | *P. mesoacidophila* MX-45 | mutB | 400 | 4.0 | 4.3 | 0.48 | 9.0 | 1.720 | n.m. | u.m. |
| pHWG315 | | mutB | 400 | 3.8 | 45.2 | 0.46 | 98.3 | 18.080 | 340 | 28.9% |
| | *P. rubrum* | smuA | 400 | 3.0 | 1.6 | 0.36 | 4.4 | 640 | n.m. | u.m. |
| pHWG314 | | smuA | 400 | 2.8 | 16.5 | 0.34 | 48.5 | 6.600 | 310 | 15.6% |
| | *P. mesoacidophila* MX-45 | mutB | 3000 | 27.2 | 28.4 | 3.26 | 8.7 | 85.200 | n.m. | u.m. |
| pHWG315 | | mutB | 3000 | 26.6 | 308.5 | 3.19 | 96.7 | 925.500 | n.m. | n.m. |
| | *P. rubrum* | smuA | 3000 | 29.5 | 14.9 | 3.54 | 4.2 | 44.700 | n.m. | u.m. |
| pHWG314 | | smuA | 3000 | 26.1 | 149.6 | 3.13 | 47.8 | 448.800 | n.m. | n.m. | n.m. = not measured
u.m. = unmeasurable

What is claimed is:

1. An isolated or purified protein with sucrose isomerase activity, wherein the protein is recombinant and is encoded by a DNA sequence comprising
   (a) A nucleotide sequence selected from SEQ ID NO:1, SEQ ID NO:2, SEQ ID NO:3, SEQ ID NO:9, SEQ ID NO:11, SEQ ID NO:13, and any of these sequences without the signal peptide-coding region;
   (b) a nucleotide sequence corresponding to the sequences from (a) within the scope of the degeneracy of the genetic code, or
   (c) a nucleotide sequence that hybridizes with a sequence from (a), (b), or both (a) and (b), wherein a positive hybridization signal is still observed after washing with a stringency of at least 1×SSC and 0.1% SDS at 55° C. for one hour;
   and wherein the protein has sucrose isomerase activity of at least 30 units/mg.

2. An isolated or purified protein with sucrose isomerase activity as claimed in claim 1, wherein the DNA sequence of claim 1 encodes a recombinant protein comprising
   an amino acid sequence selected from SEQ ID NO:4, SEQ ID NO:5, SEQ ID NO;6, SEQ ID NO:10, SEQ ID NO:12, SEQ ID NO:14, and any of these sequences without the signal peptide region.

3. A method of preparing an isolated or purified protein with sucrose isomerase activity, wherein the protein is recombinant and is encoded by a DNA sequence comprising:
   (a) a nucleotide sequence selected from SEQ ID NO:1, SEQ ID NO:2, SEQ ID NO:3, SEQ ID NO:9, SEQ ID NO:11, SEQ ID NO:13, and any of these sequences without the signal peptide-coding region;
   (b) a nucleotide sequence corresponding to the sequences from (a) within the degeneracy of the genetic code, or
   (c) a nucleotide sequence that hybridizes with a sequence from (a), (b), both (a) and (b), wherein a positive hybridization signal is still observed after washing with a stringency of at least 1×SSC and 0.1% SDS at 55° C. for one hour;
   wherein the method comprises transforming a cell with said DNA sequence or with a vector containing said DNA sequence, inducing expression of said protein with sucrose isomerase activity, and isolating said protein with sucrose isomerase activity; and wherein the protein has sucrose isomerase activity of at least 30 units/mg.

4. The method of claim 3, wherein the cell is an enterobacterial cell.

5. The method of claim 4, wherein the enterobacterial cell is an *E. coil* cell.

6. The method of claim 3, wherein the expression of the protein with sucrose isomerase activity is induced by rhamnose.

7. The method of claim 3, wherein the isolating of the protein with sucrose isomerase activity is accomplished with a cation exchange chromatography column.

8. The method of claim 6, wherein the isolating of the protein with sucrose isomerase activity is performed in one step.

9. A method of preparing an isolated or purified protein with sucrose isomerase activity, wherein the protein is recombinant and is encoded by a DNA sequence comprising:
   (a) a nucleotide sequence selected from SEQ ID NO:1, SEQ ID NO:2, SEQ ID NO:3, SEQ ID NO:9, SEQ ID NO:11, SEQ ID NO:13, and any of these sequences without the signal peptide-coding region;
   (b) a nucleotide sequence corresponding to the sequences from (a) within the degeneracy of the genetic code, or
   (c) a nucleotide sequence that hybridizes with a sequence from (a), (b), both (a) and (b), wherein a positive hybridization signal is still observed after washing with a stringency of at least 1×SSC and 0.1% SDS at 55° C. for one hour;
   wherein the method comprises transforming an *E. coil* cell with said DNA sequence or with a vector containing said DNA sequence, inducing expression of said protein with sucrose isomerase activity, and isolating said protein with sucrose isomerase activity; and wherein the protein has sucrose isomerase activity of at least 30 units/mg.

* * * * *

UNITED STATES PATENT AND TRADEMARK OFFICE
CERTIFICATE OF CORRECTION

PATENT NO. : 6,884,611 B2
DATED : April 26, 2005
INVENTOR(S) : Ralf Mattes et al.

It is certified that error appears in the above-identified patent and that said Letters Patent is hereby corrected as shown below:

Column 59,
Line 24, "SEQ ID NO; 6" should read -- SEQ ID NO: 6 --.

Signed and Sealed this

Nineteenth Day of July, 2005

JON W. DUDAS
*Director of the United States Patent and Trademark Office*

SEQUENCE LISTING (1) GENERAL INFORMATION:

(iii) NUMBER OF SEQUENCES: 26

(2) INFORMATION FOR SEQ ID NO: 1:

(i) SEQUENCE CHARACTERISTICS:
      (A) LENGTH: 1890 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO: 1:

| | | | | | | |
|---|---|---|---|---|---|---|
| ATGCCCCGTC | AAGGATTGAA | AACTGCACTA | GCGATTTTTC | TAACCACATC | ATTATGCATC | 60 |
| TCATGCCAGC | AAGCCTTCGG | TACGCAACAA | CCCTTGCTTA | ACGAAAAGAG | TATCGAACAG | 120 |
| TCGAAAACCA | TACCTAAATG | GTGGAAGGAG | GCTGTTTTTT | ATCAGGTGTA | TCCGCGCTCC | 180 |
| TTTAAAGACA | CCAACGGAGA | TGGCATCGGG | GATATTAACG | GCATCATAGA | AAAATTAGAC | 240 |
| TATCTAAAAG | CCTTGGGGAT | TGATGCCATT | TGGATCAACC | CACATTATGA | TTCTCCGAAC | 300 |
| ACGGATAATG | GTTACGATAT | ACGTGATTAT | CGAAAAATCA | TGAAAGAATA | TGGCACGATG | 360 |
| GAGGATTTTG | ACCGCCTGAT | TTCTGAAATG | AAAAAACGGA | ATATGCGGTT | GATGATTGAT | 420 |
| GTGGTCATCA | ACCACACCAG | CGATCAAAAC | GAATGGTTTG | TTAAAAGTAA | AAGCAGTAAG | 480 |
| GATAATCCTT | ATCGCGGCTA | TTATTTCTGG | AAAGATGCTA | AGAAGGGCA | GGCGCCTAAT | 540 |
| AATTACCCTT | CATTCTTTGG | TGGCTCGGCG | TGGCAAAAAG | ATGAAAAGAC | CAATCAATAC | 600 |
| TACCTGCACT | ATTTTGCTAA | ACAACAGCCT | GACCTAAACT | GGGATAATCC | CAAAGTCCGT | 660 |
| CAAGATCTTT | ATGCAATGTT | ACGTTTCTGG | TTAGATAAAG | GCGTGTCTGG | TTTACGTTTT | 720 |
| GATACGGTAG | CGACCTACTC | AAAAATTCCG | GATTTCCCAA | ATCTCACCCA | ACAACAGCTG | 780 |
| AAGAATTTTG | CAGCGGAGTA | TACCAAGGGC | CCTAATATTC | ATCGTTACGT | CAATGAAATG | 840 |
| AATAAAGAGG | TCTTGTCTCA | TTACGACATT | GCGACTGCCG | GTGAAATCTT | TGGCGTACCC | 900 |
| TTGGATCAAT | CGATAAAGTT | CTTCGATCGC | CGCCGTGATG | AGCTGAACAT | TGCATTTACC | 960 |
| TTTGACTTAA | TCAGACTCGA | TCGAGACTCT | GATCAAAGAT | GGCGTCGAAA | AGATTGGAAA | 1020 |
| TTGTCGCAAT | TCCGGCAGAT | CATCGATAAC | GTTGACCGTA | CTGCAGGAGA | ATATGGTTGG | 1080 |
| AATGCCTTCT | TCTTGGATAA | CCACGACAAT | CCGCGCGCTG | TCTCGCACTT | TGGCGATGAT | 1140 |
| GATCGCCCAC | AATGGCGTGA | GCCATCGGCT | AAAGCGCTTG | CAACCTTGAC | GCTGACTCAA | 1200 |
| CGAGCAACAC | CTTTTATTTA | TCAAGGTTCA | GAATTGGGCA | TGACCAATTA | CCCGTTTAAA | 1260 |
| GCTATTGATG | AATTCGATGA | TATTGAGGTG | AAAGGTTTTT | GGCATGACTA | CGTTGAGACA | 1320 |
| GGAAAGGTCA | AGCCGACGA | GTTCTTGCAA | AATGTACGCC | TGACGAGCAG | GGATAACAGC | 1380 |
| CGGACGCCGT | TCCAATGGGA | TGGGAGCAAA | AATGCAGGAT | TCACGAGCGG | AAAACCTTGG | 1440 |
| TTCAAGGTCA | ACCCAAACTA | CCAGGAAATC | AATGCAGTAA | GTCAAGTCAC | ACAACCCGAC | 1500 |
| TCAGTATTTA | ACTATTATCG | TCAGTTGATC | AAGATAAGGC | ATGACATCCC | GGCACTGACC | 1560 |
| TATGGTACAT | ACACCGATTT | GGATCCTGCA | ATGATTCGG | TCTACGCCTA | TACACGCAGC | 1620 |
| CTTGGGGCGG | AAAAATATCT | TGTTGTTGTT | AACTTCAAGG | AGCAAATGAT | GAGATATAAA | 1680 |
| TTACCGGATA | ATTTATCCAT | TGAGAAAGTG | ATTATAGACA | GCAACAGCAA | AACGTGGTG | 1740 |
| AAAAAGAATG | ATTCATTACT | CGAGCTAAAA | CCATGGCAGT | CAGGGGTTTA | TAAAACTAAA | 1800 |
| TCAATAAATC | TCATAGTCAC | GCCAAATAAT | GTAAATATAT | TGAAACTATT | AAAACCGGCA | 1860 |
| TTTTATGCCG | GTTTTTTTAG | CGCAAAATAG | | | | 1890 |

(2) INFORMATION FOR SEQ ID NO: 2:

(i) SEQUENCE CHARACTERISTICS:
        (A) LENGTH: 1305 base pairs
        (B) TYPE: nucleic acid
        (C) STRANDEDNESS: single
        (D) TOPOLOGY: linear (ii) MOLECULE TYPE: DNA (genomic)

(ix) FEATURE:
    (A) NAME/KEY: misc_RNA
    (B) LOCATION: 28
    (D) OTHER INFORMATION: /note= "N = Unknown"

(ix) FEATURE:
    (A) NAME/KEY: misc_RNA
    (B) LOCATION: 85..87
    (D) OTHER INFORMATION: /note= "N = Unknown"

(xi) SEQUENCE DESCRIPTION: SEQ ID NO: 2:

| | | | | | |
|---|---|---|---|---|---|
| ATGTCCTCTC | AAGGATTGAA | AACGGCTNTC | GCTATTTTTC | TTGCAACCAC | TTTTTCTGCC | 60
| ACATCCTATC | AGGCCTGCAG | TGCCNNNCCA | GATACCGCCC | CCTCACTCAC | CGTTCAGCAA | 120
| TCAAATGCCC | TGCCCACATG | GTGGAAGCAG | GCTGTTTTTT | ATCAGGTATA | TCCACGCTCA | 180
| TTTAAAGATA | CGAATGGGGA | TGGCATTGGG | GATTTAAACG | GTATTATTGA | GAATTTAGAC | 240
| TATCTGAAGA | AACTGGGTAT | TGATGCGATT | TGGATCAATC | CACATTACGA | TTCGCCGAAT | 300
| ACGGATAATG | GTTATGACAT | CCGGGATTAC | CGTAAGATAA | TGAAAGAATA | CGGTACGATG | 360
| GAAGACTTTG | ACCGTCTTAT | TTCAGAAATG | AAGAAACGCA | ATATGCGTTT | GATGATTGAT | 420
| ATTGTTATCA | ACCACACCAG | CGATCAGCAT | GCCTGGTTTG | TTCAGAGCAA | ATCGGGTAAG | 480
| AACAACCCCT | ACAGGGACTA | TTACTTCTGG | CGTGACGGTA | AGGATGGCCA | TGCCCCCAAT | 540
| AACTATCCCT | CCTTCTTCGG | TGGCTCAGCC | TGGGAAAAAG | ACGATAAATC | AGGCCAGTAT | 600
| TACCTCCATT | ACTTTGCCAA | ACAGCAACCC | GACCTCAACT | GGGACAATCC | CAAAGTCCGT | 660
| CAAGACCTGT | ATGACATGCT | CCGCTTCTGG | TTAGATAAAG | GCGTTTCTGG | TTTACGCTTT | 720
| GATACCGTTG | CCACCTACTC | GAAAATCCCG | AACTTCCCTG | ACCTTAGCCA | ACAGCAGTTA | 780
| AAAAATTTCG | CCGAGGAATA | TACTAAAGGT | CCTAAAATTC | ACGACTACGT | GAATGAAATG | 840
| AACAGAGAAG | TATTATCCCA | CTATGATATC | GCCACTGCGG | GGGAAATATT | TGGGGTTCCT | 900
| CTGGATAAAT | CGATTAAGTT | TTTCGATCGC | CGTAGAAATG | AATTAAATAT | AGCGTTTACG | 960
| TTTGATCTGA | TCAGGCTCGA | TCGTGATGCT | GATGAAAGAT | GGCGGCGAAA | AGACTGGACC | 1020
| CTTTCGCAGT | TCCGAAAAAT | TGTCGATAAG | GTTGACCAAA | CGGCAGGAGA | GTATGGGTGG | 1080
| AATGCCTTTT | TCTTAGACAA | TCACGACAAT | CCCCGCGCGG | TTTCTCACTT | TGGTGATGAT | 1140
| CGACCACAAT | GGCGCGAGCA | TGCGGCGAAA | GCACTGGCAA | CATTGACGCT | GACCCAGCGT | 1200
| GCAACGCCGT | TTATCTATCA | GGGTTCAGAA | CTCGGTATGA | CCAATTATCC | CTTTAAAAAA | 1260
| ATCGATGATT | TCGATGATGT | AGAGGTGAAA | GGTTTTTGGC | AAGAC | | 1305

(2) INFORMATION FOR SEQ ID NO: 3:

(i) SEQUENCE CHARACTERISTICS:
        (A) LENGTH: 471 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 3:

| | | | | | |
|---|---|---|---|---|---|
| GTTTTTTATC | AGATCTATCC | TCGCTCATTT | AAAGACACCA | ATGATGATGG | CATTGGCGAT | 60
| ATTCGCGGTA | TTATTGAAAA | GCTGGACTAT | CTGAAATCGC | TCGGTATTGA | CGCTATCTGG | 120
| ATCAATCCCC | ATTACGACTC | TCCGAACACC | GATAACGGCT | ATGACATCAG | TAATTATCGT | 180
| CAGATAATGA | AAGAGTATGG | CACAATGGAG | GATTTTGATA | GCCTTGTTGC | CGAAATGAAA | 240
| AAACGAAATA | TGCGCTTAAT | GATCGACGTG | GTCATTAACC | ATACCAGTGA | TCAACACCCG | 300

```
TGGTTTATTC AGAGTAAAAG CGATAAAAAC AACCCTTATC GTGACTATTA TTTCTGGCGT      360

GACGGAAAAG ATAATCAGCC ACCTAATAAT TACCCCTCAT TTTTCGGCGG CTCGGCATGG      420

CAAAAAGATG CAAAGTCAGG ACAGTACTAT TTACACTATT TTGCCAGACA G              471
```

(2) INFORMATION FOR SEQ ID NO: 4:

(i) SEQUENCE CHARACTERISTICS:
        (A) LENGTH: 629 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 4:

```
Met Pro Arg Gln Gly Leu Lys Thr Ala Leu Ala Ile Phe Leu Thr Thr
1               5                   10                  15

Ser Leu Cys Ile Ser Cys Gln Gln Ala Phe Gly Thr Gln Gln Pro Leu
            20                  25                  30

Leu Asn Glu Lys Ser Ile Glu Gln Ser Lys Thr Ile Pro Lys Trp Trp
        35                  40                  45

Lys Glu Ala Val Phe Tyr Gln Val Tyr Pro Arg Ser Phe Lys Asp Thr
    50                  55                  60

Asn Gly Asp Gly Ile Gly Asp Ile Asn Gly Ile Ile Glu Lys Leu Asp
65                  70                  75                  80

Tyr Leu Lys Ala Leu Gly Ile Asp Ala Ile Trp Ile Asn Pro His Tyr
                85                  90                  95

Asp Ser Pro Asn Thr Asp Asn Gly Tyr Asp Ile Arg Asp Tyr Arg Lys
            100                 105                 110

Ile Met Lys Glu Tyr Gly Thr Met Glu Asp Phe Asp Arg Leu Ile Ser
        115                 120                 125

Glu Met Lys Lys Arg Asn Met Arg Leu Met Ile Asp Val Val Ile Asn
    130                 135                 140

His Thr Ser Asp Gln Asn Glu Trp Phe Val Lys Ser Lys Ser Ser Lys
145                 150                 155                 160

Asp Asn Pro Tyr Arg Gly Tyr Tyr Phe Trp Lys Asp Ala Lys Glu Gly
                165                 170                 175

Gln Ala Pro Asn Asn Tyr Pro Ser Phe Phe Gly Gly Ser Ala Trp Gln
            180                 185                 190

Lys Asp Glu Lys Thr Asn Gln Tyr Tyr Leu His Tyr Phe Ala Lys Gln
        195                 200                 205

Gln Pro Asp Leu Asn Trp Asp Asn Pro Lys Val Arg Gln Asp Leu Tyr
    210                 215                 220

Ala Met Leu Arg Phe Trp Leu Asp Lys Gly Val Ser Gly Leu Arg Phe
225                 230                 235                 240

Asp Thr Val Ala Thr Tyr Ser Lys Ile Pro Asp Phe Pro Asn Leu Thr
                245                 250                 255

Gln Gln Gln Leu Lys Asn Phe Ala Ala Glu Tyr Thr Lys Gly Pro Asn
            260                 265                 270

Ile His Arg Tyr Val Asn Glu Met Asn Lys Glu Val Leu Ser His Tyr
        275                 280                 285

Asp Ile Ala Thr Ala Gly Glu Ile Phe Gly Val Pro Leu Asp Gln Ser
    290                 295                 300

Ile Lys Phe Phe Asp Arg Arg Asp Glu Leu Asn Ile Ala Phe Thr
305                 310                 315                 320
```

```
Phe Asp Leu Ile Arg Leu Asp Arg Asp Ser Asp Gln Arg Trp Arg Arg
                325                 330                 335

Lys Asp Trp Lys Leu Ser Gln Phe Arg Gln Ile Ile Asp Asn Val Asp
            340                 345                 350

Arg Thr Ala Gly Glu Tyr Gly Trp Asn Ala Phe Phe Leu Asp Asn His
                355                 360                 365

Asp Asn Pro Arg Ala Val Ser His Phe Gly Asp Asp Arg Pro Gln
            370                 375                 380

Trp Arg Glu Pro Ser Ala Lys Ala Leu Ala Thr Leu Thr Leu Thr Gln
385                 390                 395                 400

Arg Ala Thr Pro Phe Ile Tyr Gln Gly Ser Glu Leu Gly Met Thr Asn
                405                 410                 415

Tyr Pro Phe Lys Ala Ile Asp Glu Phe Asp Asp Ile Glu Val Lys Gly
                420                 425                 430

Phe Trp His Asp Tyr Val Glu Thr Gly Lys Val Lys Ala Asp Glu Phe
            435                 440                 445

Leu Gln Asn Val Arg Leu Thr Ser Arg Asp Asn Ser Arg Thr Pro Phe
        450                 455                 460

Gln Trp Asp Gly Ser Lys Asn Ala Gly Phe Thr Ser Gly Lys Pro Trp
465                 470                 475                 480

Phe Lys Val Asn Pro Asn Tyr Gln Glu Ile Asn Ala Val Ser Gln Val
                485                 490                 495

Thr Gln Pro Asp Ser Val Phe Asn Tyr Tyr Arg Gln Leu Ile Lys Ile
            500                 505                 510

Arg His Asp Ile Pro Ala Leu Thr Tyr Gly Thr Tyr Thr Asp Leu Asp
        515                 520                 525

Pro Ala Asn Asp Ser Val Tyr Ala Tyr Thr Arg Ser Leu Gly Ala Glu
            530                 535                 540

Lys Tyr Leu Val Val Asn Phe Lys Glu Gln Met Met Arg Tyr Lys
545                 550                 555                 560

Leu Pro Asp Asn Leu Ser Ile Glu Lys Val Ile Ile Asp Ser Asn Ser
            565                 570                 575

Lys Asn Val Val Lys Asn Asp Ser Leu Leu Glu Leu Lys Pro Trp
            580                 585                 590

Gln Ser Gly Val Tyr Lys Thr Lys Ser Ile Asn Leu Ile Val Thr Pro
        595                 600                 605

Asn Asn Val Asn Ile Leu Lys Leu Leu Lys Pro Ala Phe Tyr Ala Gly
        610                 615                 620

Phe Phe Ser Ala Lys
625

(2) INFORMATION FOR SEQ ID NO: 5:

(i) SEQUENCE CHARACTERISTICS:
        (A) LENGTH: 435 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 10
        (D) OTHER INFORMATION: /note= "X = Unknown"

(ix) FEATURE:
        (A) NAME/KEY: Peptide
```

(B) LOCATION: 29
(D) OTHER INFORMATION: /note= "X = Unknown"

(xi) SEQUENCE DESCRIPTION: SEQ ID NO: 5:

```
Met Ser Ser Gln Gly Leu Lys Thr Ala Xaa Ala Ile Phe Leu Ala Thr
1               5                   10                  15

Thr Phe Ser Ala Thr Ser Tyr Gln Ala Cys Ser Ala Xaa Pro Asp Thr
                20                  25                  30

Ala Pro Ser Leu Thr Val Gln Gln Ser Asn Ala Leu Pro Thr Trp Trp
            35                  40                  45

Lys Gln Ala Val Phe Tyr Gln Val Tyr Pro Arg Ser Phe Lys Asp Thr
50                  55                  60

Asn Gly Asp Gly Ile Gly Asp Leu Asn Gly Ile Ile Glu Asn Leu Asp
65                  70                  75                  80

Tyr Leu Lys Lys Leu Gly Ile Asp Ala Ile Trp Ile Asn Pro His Tyr
                85                  90                  95

Asp Ser Pro Asn Thr Asp Asn Gly Tyr Asp Ile Arg Asp Tyr Arg Lys
            100                 105                 110

Ile Met Lys Glu Tyr Gly Thr Met Glu Asp Phe Asp Arg Leu Ile Ser
        115                 120                 125

Glu Met Lys Lys Arg Asn Met Arg Leu Met Ile Asp Ile Val Ile Asn
130                 135                 140

His Thr Ser Asp Gln His Ala Trp Phe Val Gln Ser Lys Ser Gly Lys
145                 150                 155                 160

Asn Asn Pro Tyr Arg Asp Tyr Tyr Phe Trp Arg Asp Gly Lys Asp Gly
                165                 170                 175

His Ala Pro Asn Asn Tyr Pro Ser Phe Phe Gly Gly Ser Ala Trp Glu
            180                 185                 190

Lys Asp Lys Ser Gly Gln Tyr Tyr Leu His Tyr Phe Ala Lys Gln
        195                 200                 205

Gln Pro Asp Leu Asn Trp Asp Asn Pro Lys Val Arg Gln Asp Leu Tyr
        210                 215                 220

Asp Met Leu Arg Phe Trp Leu Asp Lys Gly Val Ser Gly Leu Arg Phe
225                 230                 235                 240

Asp Thr Val Ala Thr Tyr Ser Lys Ile Pro Asn Phe Pro Asp Leu Ser
                245                 250                 255

Gln Gln Gln Leu Lys Asn Phe Ala Glu Glu Tyr Thr Lys Gly Pro Lys
            260                 265                 270

Ile His Asp Tyr Val Asn Glu Met Asn Arg Glu Val Leu Ser His Tyr
        275                 280                 285

Asp Ile Ala Thr Ala Gly Glu Ile Phe Gly Val Pro Leu Asp Lys Ser
290                 295                 300

Ile Lys Phe Phe Asp Arg Arg Arg Asn Glu Leu Asn Ile Ala Phe Thr
305                 310                 315                 320

Phe Asp Leu Ile Arg Leu Asp Arg Asp Ala Asp Glu Arg Trp Arg Arg
                325                 330                 335

Lys Asp Trp Thr Leu Ser Gln Phe Arg Lys Ile Val Asp Lys Val Asp
            340                 345                 350

Gln Thr Ala Gly Glu Tyr Gly Trp Asn Ala Phe Phe Leu Asp Asn His
        355                 360                 365

Asp Asn Pro Arg Ala Val Ser His Phe Gly Asp Asp Arg Pro Gln Trp
        370                 375                 380

Arg Glu His Ala Ala Lys Ala Leu Ala Thr Leu Thr Leu Thr Gln Arg
385                 390                 395                 400
```

```
Ala Thr Pro Phe Ile Tyr Gln Gly Ser Glu Leu Gly Met Thr Asn Tyr
            405                 410                 415

Pro Phe Lys Lys Ile Asp Asp Phe Asp Asp Val Glu Val Lys Gly Phe
            420                 425                 430

Trp Gln Asp
        435

(2) INFORMATION FOR SEQ ID NO: 6:

(i) SEQUENCE CHARACTERISTICS:
        (A) LENGTH: 157 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 6:

Val Phe Tyr Gln Ile Tyr Pro Arg Ser Phe Lys Asp Thr Asn Asp Asp
1               5                   10                  15

Gly Ile Gly Asp Ile Arg Gly Ile Ile Glu Lys Leu Asp Tyr Leu Lys
            20                  25                  30

Ser Leu Gly Ile Asp Ala Ile Trp Ile Asn Pro His Tyr Asp Ser Pro
            35                  40                  45

Asn Thr Asp Asn Gly Tyr Asp Ile Ser Asn Tyr Arg Gln Ile Met Lys
            50                  55                  60

Glu Tyr Gly Thr Met Glu Asp Phe Asp Ser Leu Val Ala Glu Met Lys
65                  70                  75                  80

Lys Arg Asn Met Arg Leu Met Ile Asp Val Val Ile Asn His Thr Ser
                85                  90                  95

Asp Gln His Pro Trp Phe Ile Gln Ser Lys Ser Asp Lys Asn Asn Pro
            100                 105                 110

Tyr Arg Asp Tyr Tyr Phe Trp Arg Asp Gly Lys Asp Asn Gln Pro Pro
            115                 120                 125

Asn Asn Tyr Pro Ser Phe Phe Gly Gly Ser Ala Trp Gln Lys Asp Ala
            130                 135                 140

Lys Ser Gly Gln Tyr Tyr Leu His Tyr Phe Ala Arg Gln
145                 150                 155

(2) INFORMATION FOR SEQ ID NO: 7:

(i) SEQUENCE CHARACTERISTICS:
        (A) LENGTH: 1362 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 7:

ATGGCTACAA AAATCGTTTT AGTGGGCGCA GGCAGCGCGC AATTCGGCTA CGGCACCCTG    60

GGCGATATCT TCCAGAGCAA GACGCTGTAC GGCAGTGAAA TTGTGCTGCA TGACATCAAC   120

CCAACCTCGC TGGCCGTGAC CGAGAAAACC GCCCGTGACT TCCTGGCTGC GGAAGATCTG   180

CCGTTTATCG TCAGCGCCAC CACCGATCGC AAAACCGCGC TGAGCGGAGC GGAGTTCGTG   240

ATTATCTCCA TTGAAGTGGG CGACCGCTTT GCCCTGTGGG ATCTCGACTG CAGATCCCG    300

CAACAGTATG GCATTCAGCA GGTGTATGGT GAAAACGGTG CCCTGGCGG GCTGTTCCAC    360

TCGCTGCGCA TCATTCCACC GATCCTCGAC ATCTGCGCCG ACGTGGCGGA CATTTGCCCG   420
```

-continued

```
AACGCCTGGG TATTCAACTA CTCGAACCCG ATGAGCCGCA TTTGCACCAC CGTGCATCGC      480

CGTTTCCCGC AGCTCAACTT TGTCGGCATG TGCCATGAAA TCGCCTCACT TGAGCGTTAT      540

CTGCCAGAAA TGCTCGGCAC CTCCTTCGAC AATCTCACTC TGCGCGCTGC CGGGCTGAAC      600

CACTTCAGCG TGTTGCTGGA GGCCAGCTAT AAAGACAGCG GAAAAGACGC TTACGCCGAC      660

GTACGCGCCA AGGCACCGGA CTATTTCTCC CGTCTGCCGG CGTACAGCGA TATTCTGGCT      720

TACACCCGCA ATCACGGCAA ATTGGTGGAG ACAGAAGGCA GCACCGAACG CGATGCGCTG      780

GGCGGCAAAG ACAGCGCCTA TCCGTGGGCG GACCGCACGC TGTTCAAAGA GATCCTGGAG      840

AAGTTTCACC ATTTGCCGAT CACCGGCGAC AGCCACTTTG GCGAGTACAT CCGTTGGGCC      900

AGCGAAGTCA GCGATCACCG CGGTATCCTC GATTTCTACA CCTTCTACCG CAACTATCTG      960

GGGCATGTGC AGCCAAAAAT CGAACTGAAG CTGAAAGAAC GCGTGGTGCC GATCATGGAA     1020

GGGATCCTCA CCGATTCCGG TTATGAAGAG TCTGCGGTCA ACATTCCGAA CCAGGGATTT     1080

ATCAAGCAAC TGCCGGCGTT TATTGCCGTC GAAGTCCCGG CGATTATCGA CCGCAAGGGC     1140

GTGCACGGCA TCAAGGTCGA TATGCCTGCG GGCATCGGTG GCCTGTTGAG CAACCAGATT     1200

GCGATTCACG ATCTGACCGC CGACGCAGTG ATTGAAGGCT CGCGCGACCT GGTTATCCAG     1260

GCGCTGCTGG TGGACTCGGT CAACGATAAA TGCCGCGCGA TACCGGAACT GGTGGACGTG     1320

ATGATCTCAC GCCAGGGGCC GTGGCTCGAT TACCTGAAAT AA                        1362
```

(2) INFORMATION FOR SEQ ID NO: 8:

(i) SEQUENCE CHARACTERISTICS:
        (A) LENGTH: 453 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 8:

```
Met Ala Thr Lys Ile Val Leu Val Gly Ala Gly Ser Ala Gln Phe Gly
1               5                   10                  15

Tyr Gly Thr Leu Gly Asp Ile Phe Gln Ser Lys Thr Leu Tyr Gly Ser
            20                  25                  30

Glu Ile Val Leu His Asp Ile Asn Pro Thr Ser Leu Ala Val Thr Glu
        35                  40                  45

Lys Thr Ala Arg Asp Phe Leu Ala Ala Glu Asp Leu Pro Phe Ile Val
    50                  55                  60

Ser Ala Thr Thr Asp Arg Lys Thr Ala Leu Ser Gly Ala Glu Phe Val
65                  70                  75                  80

Ile Ile Ser Ile Glu Val Gly Asp Arg Phe Ala Leu Trp Asp Leu Asp
                85                  90                  95

Trp Gln Ile Pro Gln Gln Tyr Gly Ile Gln Gln Val Tyr Gly Glu Asn
            100                 105                 110

Gly Gly Pro Gly Gly Leu Phe His Ser Leu Arg Ile Ile Pro Pro Ile
        115                 120                 125

Leu Asp Ile Cys Ala Asp Val Ala Asp Ile Cys Pro Asn Ala Trp Val
    130                 135                 140

Phe Asn Tyr Ser Asn Pro Met Ser Arg Ile Cys Thr Thr Val His Arg
145                 150                 155                 160

Arg Phe Pro Gln Leu Asn Phe Val Gly Met Cys His Glu Ile Ala Ser
                165                 170                 175
```

-continued

```
Leu Glu Arg Tyr Leu Pro Glu Met Leu Gly Thr Ser Phe Asp Asn Leu
            180                 185                 190

Thr Leu Arg Ala Ala Gly Leu Asn His Phe Ser Val Leu Leu Glu Ala
        195                 200                 205

Ser Tyr Lys Asp Ser Gly Lys Asp Ala Tyr Ala Asp Val Arg Ala Lys
    210                 215                 220

Ala Pro Asp Tyr Phe Ser Arg Leu Pro Gly Tyr Ser Asp Ile Leu Ala
225                 230                 235                 240

Tyr Thr Arg Asn His Gly Lys Leu Val Glu Thr Gly Ser Thr Glu
                245                 250                 255

Arg Asp Ala Leu Gly Gly Lys Asp Ser Ala Tyr Pro Trp Ala Asp Arg
            260                 265                 270

Thr Leu Phe Lys Glu Ile Leu Glu Lys Phe His His Leu Pro Ile Thr
            275                 280                 285

Gly Asp Ser His Phe Gly Glu Tyr Ile Arg Trp Ala Ser Glu Val Ser
290                 295                 300

Asp His Arg Gly Ile Leu Asp Phe Tyr Thr Phe Tyr Arg Asn Tyr Leu
305                 310                 315                 320

Gly His Val Gln Pro Lys Ile Glu Leu Lys Leu Lys Glu Arg Val Val
                325                 330                 335

Pro Ile Met Glu Gly Ile Leu Thr Asp Ser Gly Tyr Glu Glu Ser Ala
            340                 345                 350

Val Asn Ile Pro Asn Gln Gly Phe Ile Lys Gln Leu Pro Ala Phe Ile
        355                 360                 365

Ala Val Glu Val Pro Ala Ile Ile Asp Arg Lys Gly Val His Gly Ile
    370                 375                 380

Lys Val Asp Met Pro Ala Gly Ile Gly Gly Leu Leu Ser Asn Gln Ile
385                 390                 395                 400

Ala Ile His Asp Leu Thr Ala Asp Ala Val Ile Glu Gly Ser Arg Asp
                405                 410                 415

Leu Val Ile Gln Ala Leu Leu Val Asp Ser Val Asn Asp Lys Cys Arg
            420                 425                 430

Ala Ile Pro Glu Leu Val Asp Val Met Ile Ser Arg Gln Gly Pro Trp
        435                 440                 445

Leu Asp Tyr Leu Lys
    450
```

(2) INFORMATION FOR SEQ ID NO: 9:

(i) SEQUENCE CHARACTERISTICS:
        (A) LENGTH: 1803 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 9:

```
ATGCCCCGTC AAGGATTGAA AACTGCACTA GCGATTTTTC TAACCACATC ATTATGCATC      60

TCATGCCAGC AAGCCTTCGG TACGCAACAA CCCTTGCTTA ACGAAAAGAG TATCGAACAG     120

TCGAAAACCA TACCTAAATG GTGGAAGGAG GCTGTTTTTT ATCAGGTGTA TCCGCGCTCC     180

TTTAAAGACA CCAACGGAGA TGGCATCGGG GATATTAACG GCATCATAGA AAAATTAGAC     240

TATCTAAAAG CCTTGGGGAT TGATGCCATT TGGATCAACC CACATTATGA TTCTCCGAAC     300

ACGGATAATG GTTACGATAT ACGTGATTAT CGAAAAATCA TGAAAGAATA TGGCACGATG     360
```

```
GAGGATTTTG ACCGCCTGAT TTCTGAAATG AAAAAACGGA ATATGCGGTT GATGATTGAT      420

GTGGTCATCA ACCACACCAG CGATCAAAAC GAATGGTTTG TTAAAAGTAA AAGCAGTAAG      480

GATAATCCTT ATCGCGGCTA TTATTTCTGG AAAGATGCTA AGAAGGGCA GGCGCCTAAT       540

AATTACCCTT CATTCTTTGG TGGCTCGGCG TGGCAAAAAG ATGAAAAGAC CAATCAATAC      600

TACCTGCACT ATTTTGCTAA ACAACAGCCT GACCTAAACT GGGATAATCC CAAAGTCCGC      660

CAAGATCTTT ATGCAATGTT ACGTTTCTGG TTAGATAAAG GCGTGTCTGG TTTACGTTTT      720

GATACGGTAG CGACCTACTC AAAAATTCCG GATTTCCCAA ATCTCACCCA ACAACAGCTG      780

AAGAATTTTG CAGCGGAGTA TACCAAGGGC CCTAATATTC ATCGTTACGT CAATGAAATG      840

AATAAAGAGG TCTTGTCTCA TTACGACATT GCGACTGCCG GTGAAATCTT TGGCGTACCC      900

TTGGATCAAT CGATAAAGTT CTTCGATCGC CGCCGTGATG AGCTGAACAT TGCATTTACC      960

TTTGACTTAA TCAGACTCGA TCGAGACTCT GATCAAAGAT GGCGTCGAAA AGATTGGAAA     1020

TTGTCGCAAT TCCGGCAGAT CATCGATAAC GTTGACCGTA CTGCAGGAGA ATATGGTTGG     1080

AATGCCTTCT TCTTGGATAA CCACGACAAT CCGCGCGCTG TCTCGCACTT TGGCGATGAT     1140

CGCCCACAAT GGCGTGAGCC ATCGGCTAAA GCGCTTGCAA CCTTGACGCT GACTCAACGA     1200

GCAACACCTT TTATTTATCA AGGTTCAGAA TTGGGCATGA CCAATTACCC GTTTAAAGCT     1260

ATTGATGAAT TCGATGATAT TGAGGTGAAA GGTTTTTGGC ATGACTACGT TGAGACAGGA     1320

AAGGTCAAAG CCGACGAGTT CTTGCAAAAT GTACGCCTGA CGAGCAGGGA TAACAGCCGG     1380

ACGCCGTTCC AATGGGATGG GAGCAAAAAT GCAGGATTCA CGAGCGGAAA ACCTTGGTTC     1440

AAGGTCAACC CAAACTACCA GGAAATCAAT GCAGTAAGTC AAGTCACACA ACCCGACTCA     1500

GTATTTAACT ATTATCGTCA GTTGATCAAG ATAAGGCATG ACATCCCGGC ACTGACCTAT     1560

GGTACATACA CCGATTTGGA TCCTGCAAAT GATTCGGTCT ACGCCTATAC ACGCAGCCTT     1620

GGGGCGGAAA AATATCTTGT TGTTGTTAAC TTCAAGGAGC AAATGATGAG ATATAAATTA     1680

CCGGATAATT TATCCATTGA GAAAGTGATT ATAGACAGCA ACAGCAAAAA CGTGGTGAAA     1740

AAGAATGATT CATTACTCGA GCTAAAACCA TGGCAGTCAG GGGTTTATAA ACTAAATCAA     1800

TAA                                                                  1803
```

(2) INFORMATION FOR SEQ ID NO: 10:

(i) SEQUENCE CHARACTERISTICS:
        (A) LENGTH: 600 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 10:

```
Met Pro Arg Gln Gly Leu Lys Thr Ala Leu Ala Ile Phe Leu Thr Thr
1               5                   10                  15

Ser Leu Cys Ile Ser Cys Gln Gln Ala Phe Gly Thr Gln Gln Pro Leu
            20                  25                  30

Leu Asn Glu Lys Ser Ile Glu Gln Ser Lys Thr Ile Pro Lys Trp Trp
        35                  40                  45

Lys Glu Ala Val Phe Tyr Gln Val Tyr Pro Arg Ser Phe Lys Asp Thr
    50                  55                  60

Asn Gly Asp Gly Ile Gly Asp Ile Asn Gly Ile Ile Glu Lys Leu Asp
65                  70                  75                  80

Tyr Leu Lys Ala Leu Gly Ile Asp Ala Ile Trp Ile Asn Pro His Tyr
```

-continued

```
                85                  90                  95
Asp Ser Pro Asn Thr Asp Asn Gly Tyr Asp Ile Arg Asp Tyr Arg Lys
            100                 105                 110
Ile Met Lys Glu Tyr Gly Thr Met Glu Asp Phe Asp Arg Leu Ile Ser
            115                 120                 125
Glu Met Lys Lys Arg Asn Met Arg Leu Met Ile Asp Val Val Ile Asn
130                 135                 140
His Thr Ser Asp Gln Asn Glu Trp Phe Val Lys Ser Lys Ser Lys
145                 150                 155                 160
Asp Asn Pro Tyr Arg Gly Tyr Tyr Phe Trp Lys Asp Ala Lys Glu Gly
            165                 170                 175
Gln Ala Pro Asn Asn Tyr Pro Ser Phe Phe Gly Gly Ser Ala Trp Gln
            180                 185                 190
Lys Asp Glu Lys Thr Asn Gln Tyr Tyr Leu His Tyr Phe Ala Lys Gln
            195                 200                 205
Gln Pro Asp Leu Asn Trp Asp Asn Pro Lys Val Arg Gln Asp Leu Tyr
            210                 215                 220
Ala Met Leu Arg Phe Trp Leu Asp Lys Gly Val Ser Gly Leu Arg Phe
225                 230                 235                 240
Asp Thr Val Ala Thr Tyr Ser Lys Ile Pro Asp Phe Pro Asn Leu Thr
            245                 250                 255
Gln Gln Gln Leu Lys Asn Phe Ala Ala Glu Tyr Thr Lys Gly Pro Asn
            260                 265                 270
Ile His Arg Tyr Val Asn Glu Met Asn Lys Glu Val Leu Ser His Tyr
            275                 280                 285
Asp Ile Ala Thr Ala Gly Glu Ile Phe Gly Val Pro Leu Asp Gln Ser
            290                 295                 300
Ile Lys Phe Phe Asp Arg Arg Arg Asp Glu Leu Asn Ile Ala Phe Thr
305                 310                 315                 320
Phe Asp Leu Ile Arg Leu Asp Arg Asp Ser Asp Gln Arg Trp Arg Arg
            325                 330                 335
Lys Asp Trp Lys Leu Ser Gln Phe Arg Gln Ile Ile Asp Asn Val Asp
            340                 345                 350
Arg Thr Ala Gly Glu Tyr Gly Trp Asn Ala Phe Phe Leu Asp Asn His
            355                 360                 365
Asp Asn Pro Arg Ala Val Ser His Phe Gly Asp Asp Arg Pro Gln Trp
            370                 375                 380
Arg Glu Pro Ser Ala Lys Ala Leu Ala Thr Leu Thr Leu Thr Gln Arg
385                 390                 395                 400
Ala Thr Pro Phe Ile Tyr Gln Gly Ser Glu Leu Gly Met Thr Asn Tyr
            405                 410                 415
Pro Phe Lys Ala Ile Asp Glu Phe Asp Asp Ile Glu Val Lys Gly Phe
            420                 425                 430
Trp His Asp Tyr Val Glu Thr Gly Lys Val Lys Ala Asp Glu Phe Leu
            435                 440                 445
Gln Asn Val Arg Leu Thr Ser Arg Asp Asn Ser Arg Thr Pro Phe Gln
            450                 455                 460
Trp Asp Gly Ser Lys Asn Ala Gly Phe Thr Ser Gly Lys Pro Trp Phe
465                 470                 475                 480
Lys Val Asn Pro Asn Tyr Gln Glu Ile Asn Ala Val Ser Gln Val Thr
            485                 490                 495
Gln Pro Asp Ser Val Phe Asn Tyr Tyr Arg Gln Leu Ile Lys Ile Arg
            500                 505                 510
```

```
His Asp Ile Pro Ala Leu Thr Tyr Gly Thr Tyr Thr Asp Leu Asp Pro
        515                 520                 525

Ala Asn Asp Ser Val Tyr Ala Tyr Thr Arg Ser Leu Gly Ala Glu Lys
        530                 535                 540

Tyr Leu Val Val Val Asn Phe Lys Glu Gln Met Met Arg Tyr Lys Leu
545                 550                 555                 560

Pro Asp Asn Leu Ser Ile Glu Lys Val Ile Ile Asp Ser Asn Ser Lys
                565                 570                 575

Asn Val Val Lys Lys Asn Asp Ser Leu Leu Glu Leu Lys Pro Trp Gln
        580                 585                 590

Ser Gly Val Tyr Lys Leu Asn Gln
        595                 600

(2) INFORMATION FOR SEQ ID NO: 11:

(i) SEQUENCE CHARACTERISTICS:
        (A) LENGTH: 1794 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_RNA
        (B) LOCATION: 810
        (D) OTHER INFORMATION: /note= "D = Unknown"

(ix) FEATURE:
        (A) NAME/KEY: misc_RNA
        (B) LOCATION: 1471
        (D) OTHER INFORMATION: /note= "S = Unknown"

(xi) SEQUENCE DESCRIPTION: SEQ ID NO: 11:

ATGTCTTTTG TTACGCTACG TACCGGGGTG GCTGTCGCGC TGTCATCTTT GATAATAAGT      60

CTGGCCTGCC CGGCTGTCAG TGCTGCACCA TCCTTGAATC AGGATATTCA CGTTCAAAAG     120

GAAAGTGAAT ATCCTGCATG GTGGAAAGAA GCTGTTTTTT ATCAGATCTA TCCTCGCTCA     180

TTTAAAGACA CCAATGATGA TGGCATTGGC GATATTCGCG GTATTATTGA AAAGCTGGAC     240

TATCTGAAAT CGCTCGGTAT TGACGCTATC TGGATCAATC CCCATTACGA CTCTCCGAAC     300

ACCGATAACG GCTATGACAT CAGTAATTAT CGTCAGATAA TGAAAGAGTA TGGCACAATG     360

GAGGATTTTG ATAGCCTTGT TGCCGAAATG AAAAAACGAA ATATGCGCTT AATGATCGAC     420

GTGGTCATTA ACCATACCAG TGATCAACAC CCGTGGTTTA TTCAGAGTAA AAGCGATAAA     480

AACAACCCTT ATCGTGACTA TTATTTCTGG CGTGACGGAA AAGATAATCA GCCACCTAAT     540

AATTACCCCT CATTTTTCGG CGGCTCGGCA TGGCAAAAAG ATGCAAAGTC AGGACAGTAC     600

TATTTACACT ATTTTGCCAG ACAGCAACCT GATCTCAACT GGGATAACCC GAAAGTACGT     660

GAGGATCTTT ACGCAATGCT CCGCTTCTGG CTGGATAAAG GCGTTTCAGG CATGCGATTT     720

GATACGGTGG CAACTTATTC CAAAATCCCG GGATTTCCCA ATCTGACACC TGAACAACAG     780

AAAAATTTTG CTGAACAATA CACCATGGGD CCTAATATTC ATCGATACAT TCAGGAAATG     840

AACCGGAAAG TTCTGTCCCG GTATGATGTG GCCACCGCGG GTGAAATTTT TGGCGTCCCG     900

CTGGATCGTT CGTCGCAGTT TTTTGATCGC CGCCGACATG AGCTGAATAT GGCGTTTATG     960

TTTGACCTCA TTCGTCTCGA TCGCGACAGC AATGAACGCT GGCGTCACAA GTCGTGGTCG    1020

CTCTCTCAGT TCCGCCAGAT CATCAGCAAA ATGGATGTCA CGGTCGGAAA GTATGGCTGG    1080

AACACGTTCT TCTTAGACAA CCATGACAAC CCCCGTGCGG TATCTCACTT CGGGGATGAC    1140
```

-continued

```
AGGCCGCAAT GGCGGGAGGC GTCGGCTAAG GCACTGGCGA CGATTACCCT CACTCAGCGG      1200

GCGACGCCGT TTATTTATCA GGGTTCAGAG CTGGGAATGA CTAATTATCC CTTCAGGCAA      1260

CTCAACGAAT TTGACGACAT CGAGGTCAAA GGTTTCTGGC AGGATTATGT CCAGAGTGGA      1320

AAAGTCACGG CCACAGAGTT TCTCGATAAT GTGCGCCTGA CGAGCCGCGA TAACAGCAGA      1380

ACACCTTTCC AGTGGAATGA CACCCTGAAT GCTGGTTTTA CTCGCGGAAA GCCGTGGTTT      1440

CACATCAACC CAAACTATGT GGAGATCAAC SCCGAACGCG AAGAAACCCG CGAAGATTCA      1500

GTGCTGAATT ACTATAAAAA AATGATTCAG CTACGCCACC ATATCCCTGC TCTGGTATAT      1560

GGCGCCTATC AGGATCTTAA TCCACAGGAC AATACCGTTT ATGCCTATAC CCGAACGCTG      1620

GGTAACGAGC GTTATCTGGT CGTGGTGAAC TTTAAGGAGT ACCCGGTCCG CTATACTCTC      1680

CCGGCTAATG ATGCCATCGA GGAAGTGGTC ATTGATACTC AGCAGCAAGG TGCGCCGCAC      1740

AGCACATCCC TGTCATTGAG CCCCTGGCAG GCAGGTGCGT ATAAGCTGCG GTAA           1794
```

(2) INFORMATION FOR SEQ ID NO: 12:

(i) SEQUENCE CHARACTERISTICS:
        (A) LENGTH: 597 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 270
        (D) OTHER INFORMATION: /note= "X = Unknown"

(ix) FEATURE:
        (A) NAME/KEY: Peptide
        (B) LOCATION: 491
        (D) OTHER INFORMATION: /note= "X = Unknown"

(xi) SEQUENCE DESCRIPTION: SEQ ID NO: 12:

```
Met Ser Phe Val Thr Leu Arg Thr Gly Val Ala Val Ala Leu Ser Ser
1               5                   10                  15

Leu Ile Ile Ser Leu Ala Cys Pro Ala Val Ser Ala Ala Pro Ser Leu
            20                  25                  30

Asn Gln Asp Ile His Val Gln Lys Glu Ser Glu Tyr Pro Ala Trp Trp
        35                  40                  45

Lys Glu Ala Val Phe Tyr Gln Ile Tyr Pro Arg Ser Phe Lys Asp Thr
50                  55                  60

Asn Asp Asp Gly Ile Gly Asp Ile Arg Gly Ile Ile Glu Lys Leu Asp
65                  70                  75                  80

Tyr Leu Lys Ser Leu Gly Ile Asp Ala Ile Trp Ile Asn Pro His Tyr
                85                  90                  95

Asp Ser Pro Asn Thr Asp Asn Gly Tyr Asp Ile Ser Asn Tyr Arg Gln
            100                 105                 110

Ile Met Lys Glu Tyr Gly Thr Met Glu Asp Phe Asp Ser Leu Val Ala
        115                 120                 125

Glu Met Lys Lys Arg Asn Met Arg Leu Met Ile Asp Val Val Ile Asn
    130                 135                 140

His Thr Ser Asp Gln His Pro Trp Phe Ile Gln Ser Lys Ser Asp Lys
145                 150                 155                 160

Asn Asn Pro Tyr Arg Asp Tyr Tyr Phe Trp Arg Asp Gly Lys Asp Asn
                165                 170                 175
```

```
Gln Pro Pro Asn Asn Tyr Pro Ser Phe Phe Gly Gly Ser Ala Trp Gln
                180                 185                 190

Lys Asp Ala Lys Ser Gly Gln Tyr Tyr Leu His Tyr Phe Ala Arg Gln
            195                 200                 205

Gln Pro Asp Leu Asn Trp Asp Asn Pro Lys Val Arg Glu Asp Leu Tyr
        210                 215                 220

Ala Met Leu Arg Phe Trp Leu Asp Lys Gly Val Ser Gly Met Arg Phe
225                 230                 235                 240

Asp Thr Val Ala Thr Tyr Ser Lys Ile Pro Gly Phe Pro Asn Leu Thr
                245                 250                 255

Pro Glu Gln Gln Lys Asn Phe Ala Glu Gln Tyr Thr Met Xaa Pro Asn
            260                 265                 270

Ile His Arg Tyr Ile Gln Glu Met Asn Arg Lys Val Leu Ser Arg Tyr
        275                 280                 285

Asp Val Ala Thr Ala Gly Glu Ile Phe Gly Val Pro Leu Asp Arg Ser
        290                 295                 300

Ser Gln Phe Phe Asp Arg Arg His Glu Leu Asn Met Ala Phe Met
305                 310                 315                 320

Phe Asp Leu Ile Arg Leu Asp Arg Asp Ser Asn Glu Arg Trp Arg His
                325                 330                 335

Lys Ser Trp Ser Leu Ser Gln Phe Arg Gln Ile Ile Ser Lys Met Asp
            340                 345                 350

Val Thr Val Gly Lys Tyr Gly Trp Asn Thr Phe Phe Leu Asp Asn His
        355                 360                 365

Asp Asn Pro Arg Ala Val Ser His Phe Gly Asp Asp Arg Pro Gln Trp
        370                 375                 380

Arg Glu Ala Ser Ala Lys Ala Leu Ala Thr Ile Thr Leu Thr Gln Arg
385                 390                 395                 400

Ala Thr Pro Phe Ile Tyr Gln Gly Ser Glu Leu Gly Met Thr Asn Typ
                405                 410                 415

Pro Phe Arg Gln Leu Asn Glu Phe Asp Asp Ile Glu Val Lys Gly Phe
            420                 425                 430

Trp Gln Asp Tyr Val Gln Ser Gly Lys Val Thr Ala Thr Glu Phe Leu
        435                 440                 445

Asp Asn Val Arg Leu Thr Ser Arg Asp Asn Ser Arg Thr Pro Phe Gln
        450                 455                 460

Trp Asn Asp Thr Leu Asn Ala Gly Phe Thr Arg Gly Lys Pro Trp Phe
465                 470                 475                 480

His Ile Asn Pro Asn Tyr Val Glu Ile Asn Xaa Glu Arg Glu Glu Thr
                485                 490                 495

Arg Glu Asp Ser Val Leu Asn Tyr Tyr Lys Lys Met Ile Gln Leu Arg
            500                 505                 510

His His Ile Pro Ala Leu Val Tyr Gly Ala Tyr Gln Asp Leu Asn Pro
        515                 520                 525

Gln Asp Asn Thr Val Tyr Ala Tyr Thr Arg Thr Leu Gly Asn Glu Arg
        530                 535                 540

Tyr Leu Val Val Val Asn Phe Lys Glu Tyr Pro Val Arg Tyr Thr Leu
545                 550                 555                 560

Pro Ala Asn Asp Ala Ile Glu Glu Val Val Ile Asp Thr Gln Gln Gln
                565                 570                 575

Gly Ala Pro His Ser Thr Ser Leu Ser Leu Ser Pro Trp Gln Ala Gly
            580                 585                 590

Ala Tyr Lys Leu Arg
```

-continued

595

(2) INFORMATION FOR SEQ ID NO: 13:

(i) SEQUENCE CHARACTERISTICS:
        (A) LENGTH: 1782 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_RNA
        (B) LOCATION: 1237..1331
        (D) OTHER INFORMATION: /note= "N = Unknown"

(xi) SEQUENCE DESCRIPTION: SEQ ID NO: 13:

| | | | | | |
|---|---|---|---|---|---|
| ATGCTTATGA | AGAGATTATT | CGCCGCGTCT | CTGATGCTTG | CTTTTTCAAG | CGTCTCCTCT | 60 |
| GTGAGGGCTG | AGGAGGCCGT | AAAGCCGGGC | GCGCCATGGT | GGAAAAGTGC | TGTCTTCTAT | 120 |
| CAGGTCTATC | CGCGCTCGTT | CAAGGATACC | AACGGTGATG | GGATCGGCGA | TTTCAAAGGA | 180 |
| CTGACGGAGA | AGCTCGACTA | TCTCAAGGGG | CTCGGCATAG | ACGCCATCTG | GATCAATCCA | 240 |
| CATTACGCGT | CTCCCAACAC | CGATAATGGC | TACGATATCA | GCGACTATCG | AGAGGTCATG | 300 |
| AAGGAATATG | GGACGATGGA | GGACTTCGAT | CGTCTGATGG | CTGAGTTGAA | GAAGCGCGGC | 360 |
| ATGCGGCTCA | TGGTTGATGT | CGTGATCAAC | CATTCGAGTG | ACCAACACGA | ATGGTTCAAG | 420 |
| AGCAGCCGGG | CCTCCAAAGA | CAATCCCTAC | CGTGACTATT | ATTTCTGGCG | TGACGGCAAA | 480 |
| GACGGTCACG | AGCCAAACAA | TTACCCTTCC | TTCTTCGGCG | GTTCGGCATG | GGAGAAGGAC | 540 |
| CCCGTAACCG | GCAATATTA | CCTGCATTAT | TTCGGTCGTC | AGCAGCCAGA | TCTGAACTGG | 600 |
| GACACGCCGA | AGCTTCGCGA | GGAACTCTAT | GCGATGCTGC | GGTTCTGGCT | CGACAAGGGC | 660 |
| GTATCAGGCA | TGCGGTTCGA | TACGGTGGCT | ACCTACTCGA | AGACACCGGG | TTTCCCGGAT | 720 |
| CTGACACCGG | AGCAGATGAA | GAACTTCGCG | GAGGCCTATA | CCCAGGGGCC | GAACCTTCAT | 780 |
| CGTTACCTGC | AGGAAATGCA | CGAGAAGGTC | TTCGATCATT | ATGACGCGGT | CACGGCCGGC | 840 |
| GAAATCTTCG | GCGCTCCGCT | CAATCAAGTG | CCGCTGTTCA | TCGACAGCCG | GAGGAAAGAG | 900 |
| CTGGATATGG | CTTTCACCTT | CGATCTGATC | CGTTATGATC | GCGCACTGGA | TCGTTGGCAT | 960 |
| ACCATTCCGC | GTACCTTAGC | GGACTTCCGT | CAAACGATCG | ATAAGGTCGA | CGCCATCGCG | 1020 |
| GGCGAATATG | GCTGGAACAC | GTTCTTCCTC | GGCAATCACG | ACAATCCCCG | TGCGGTATCG | 1080 |
| CATTTTGGTG | ACGATCGGCC | GCAATGGCGC | GAAGCCTCGG | CCAAGGCTCT | GGCCACCGTC | 1140 |
| ACCTTGACCC | AGCGAGGAAC | GCCGTTCATC | TTCCAAGGAG | ATGAACTCGG | AATGACCAAC | 1200 |
| TACCCCTTCA | AGACGCTGCA | GGACTTTGAT | GATATCNNNN | NNNNNNNNNN | NNNNNNNNNN | 1260 |
| NNNNNNNNNN | NNNNNNNNNN | NNNNNNNNNN | NNNNNNNNNN | NNNNNNNNNN | NNNNNNNNNN | 1320 |
| NNNNNNNNNN | NTGTGGCGTT | GACTAGCCGA | GCAAACGCCC | GCACGCCCTT | TCAATGGGAT | 1380 |
| GACAGTGCTA | ATGCGGGATT | CACAACTGGC | AAGCCTTGGC | TAAAGGTCAA | TCCAAACTAC | 1440 |
| ACTGAGATCA | ACGCCGCGCG | GGAAATTGGC | GATCCTAAAT | CGGTCTACAG | CTTTTACCGC | 1500 |
| AACCTGATCT | CAATCCGGCA | TGAAACTCCC | GCTCTTTCGA | CCGGGAGCTA | TCGCGACATC | 1560 |
| GATCCGAGTA | ATGCCGATGT | CTATGCCTAT | ACGCGCAGCC | AGGATGGCGA | GACCTATCTG | 1620 |
| GTCGTAGTCA | ACTTCAAGGC | AGAGCCAAGG | AGTTTCACGC | TTCCGGACGG | CATGCATATT | 1680 |
| GCCGAAACCC | TGATTGAGAG | CAGTTCGCCA | GCAGCTCCGG | CGGCGGGGGC | TGCAAGCCTT | 1740 |
| GAGCTGCAGC | CTTGGCAGTC | CGGCATCTAC | AAGGTGAAGT | AA | | 1782 |

(2) INFORMATION FOR SEQ ID NO: 14:

(i) SEQUENCE CHARACTERISTICS:
        (A) LENGTH: 593 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 413..444
        (D) OTHER INFORMATION: /note= "Xaa = Unknown"

(xi) SEQUENCE DESCRIPTION: SEQ ID NO: 14:

```
Met Leu Met Lys Arg Leu Phe Ala Ala Ser Leu Met Leu Ala Phe Ser
 1               5                  10                  15

Ser Val Ser Ser Val Arg Ala Glu Glu Ala Val Lys Pro Gly Ala Pro
             20                  25                  30

Trp Trp Lys Ser Ala Val Phe Tyr Gln Val Tyr Pro Arg Ser Phe Lys
         35                  40                  45

Asp Thr Asn Gly Asp Gly Ile Gly Asp Phe Lys Gly Leu Thr Glu Lys
     50                  55                  60

Leu Asp Tyr Leu Lys Gly Leu Gly Ile Asp Ala Ile Trp Ile Asn Pro
65                  70                  75                  80

His Tyr Ala Ser Pro Asn Thr Asp Asn Gly Tyr Asp Ile Ser Asp Tyr
                 85                  90                  95

Arg Glu Val Met Lys Glu Tyr Gly Thr Met Glu Asp Phe Asp Arg Leu
            100                 105                 110

Met Ala Glu Leu Lys Lys Arg Gly Met Arg Leu Met Val Asp Val Val
        115                 120                 125

Ile Asn His Ser Ser Asp Gln His Glu Trp Phe Lys Ser Ser Arg Ala
    130                 135                 140

Ser Lys Asp Asn Pro Tyr Arg Asp Tyr Tyr Phe Trp Arg Asp Gly Lys
145                 150                 155                 160

Asp Gly His Glu Pro Asn Asn Tyr Pro Ser Phe Phe Gly Gly Ser Ala
                165                 170                 175

Trp Glu Lys Asp Pro Val Thr Gly Gln Tyr Tyr Leu His Tyr Phe Gly
            180                 185                 190

Arg Gln Gln Pro Asp Leu Asn Trp Asp Thr Pro Lys Leu Arg Glu Glu
        195                 200                 205

Leu Tyr Ala Met Leu Arg Phe Trp Leu Asp Lys Gly Val Ser Gly Met
    210                 215                 220

Arg Phe Asp Thr Val Ala Thr Tyr Ser Lys Thr Pro Gly Phe Pro Asp
225                 230                 235                 240

Leu Thr Pro Glu Gln Met Leu Asn Phe Ala Glu Ala Tyr Thr Gln Gly
                245                 250                 255

Pro Asn Leu His Arg Tyr Leu Gln Glu Met His Glu Lys Val Phe Asp
            260                 265                 270

His Tyr Asp Ala Val Thr Ala Gly Glu Ile Phe Gly Ala Pro Leu Asn
        275                 280                 285

Gln Val Pro Leu Phe Ile Asp Ser Arg Arg Lys Glu Leu Asp Met Ala
    290                 295                 300

Phe Thr Phe Asp Leu Ile Arg Tyr Asp Arg Ala Leu Asp Arg Trp His
305                 310                 315                 320
```

```
Thr Ile Pro Arg Thr Leu Ala Asp Phe Arg Gln Thr Ile Asp Lys Val
            325                 330                 335

Asp Ala Ile Ala Gly Glu Tyr Gly Trp Asn Thr Phe Phe Leu Gly Asn
            340                 345                 350

His Asp Asn Pro Arg Ala Val Ser His Phe Gly Asp Asp Arg Pro Gln
            355                 360                 365

Trp Arg Glu Ala Ser Ala Lys Ala Leu Ala Thr Val Thr Leu Thr Gln
            370                 375                 380

Arg Gly Thr Pro Phe Ile Phe Gln Gly Asp Glu Leu Gly Met Thr Asn
385                 390                 395                 400

Tyr Pro Phe Lys Thr Leu Gln Asp Phe Asp Asp Ile Xaa Xaa Xaa Xaa
            405                 410                 415

Xaa Xaa Xaa Xaa Xaa Xaa Xaa Xaa Xaa Xaa Xaa Xaa Xaa Xaa Xaa Xaa
            420                 425                 430

Xaa Xaa Xaa Xaa Xaa Xaa Xaa Xaa Xaa Xaa Xaa Xaa Val Ala Leu Thr
            435                 440                 445

Ser Arg Ala Asn Ala Arg Thr Pro Phe Gln Trp Asp Asp Ser Ala Asn
            450                 455                 460

Ala Gly Phe Thr Thr Gly Lys Pro Trp Leu Lys Val Asn Pro Asn Tyr
465                 470                 475                 480

Thr Glu Ile Asn Ala Ala Arg Glu Ile Gly Asp Pro Lys Ser Val Tyr
            485                 490                 495

Ser Phe Tyr Arg Asn Leu Ile Ser Ile Arg His Glu Thr Pro Ala Leu
            500                 505                 510

Ser Thr Gly Ser Tyr Arg Asp Ile Asp Pro Ser Asn Ala Asp Val Tyr
            515                 520                 525

Ala Tyr Thr Arg Ser Gln Asp Gly Glu Thr Tyr Leu Val Val Val Asn
            530                 535                 540

Phe Lys Ala Glu Pro Arg Ser Phe Thr Leu Pro Asp Gly Met His Ile
545                 550                 555                 560

Ala Glu Thr Leu Ile Glu Ser Ser Pro Ala Ala Pro Ala Ala Gly
            565                 570                 575

Ala Ala Ser Leu Glu Leu Gln Pro Trp Gln Ser Gly Ile Tyr Lys Val
            580                 585                 590

Lys (2) INFORMATION FOR SEQ ID NO: 15:

(i) SEQUENCE CHARACTERISTICS:
        (A) LENGTH: 1704 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 15:

ATGACTGAAA AGTTATCCTT CGAGTCGACA ACAATCTCGC GTCGCTGGTG GAAAGAGGCT      60

GTTGTCTATC AGGTGTATCC CCGCTCGTTC CAGGATTCGA ACGGGGACGG CATCGGCGAC     120

CTTCCGGGCA TAACTGCGAG GCTAGATTAC ATCCTCGGTC TAGGCGTTAG TGTCATCTGG     180

CTCAGCCCCC ATTTCGACTC TCCGAATGCT GACAACGGCT ACGATATCCG TGACTATCGC     240

AAGGTGATGC GCGAATTCGG CACCATGGCG GATTTCGATC ACCTGCTGGC CGAGACGAAA     300

AAGCGCGGCA TGCGGCTGAT CATCGATCTC GTCGTCAACC ATACCAGCGA CGAGCATGTC     360

TGGTTTGCCG AAAGCCGGGC CTCGAAAAAC AGCCCGTACC GTGATTACTA CATCTGGCAT     420
```

```
CCCGGCCGGG ACGGCGCCGA GCCGAACGAC TGGCGCTCAT TTTTCTCGGG CTCGGCATGG    480
ACTTTCGACC AGCCAACCGG CGAATACTAC ATGCATCTTT TCGCCGATAA ACAGCCGGAT    540
ATCAACTGGG ACAATCCGGC TGTGCGCGCC GATGTCTATG ACATCATGCG CTTTTGGCTG    600
GACAAGGGCG TCGACGGATT CCGCATGGAT GTCATCCCCT TCATCTCCAA GCAAGACGGC    660
CTGCCCGACT ATCCTGACCA TCATCGCGGC GCGCCGCAGT TTTTCCACGG TTCGGGTCCC    720
CGCTTGCACG ACTATCTTCA GGAAATGAAC CGCGAGGTAT TGTCGCATTA CGATGTGATG    780
ACGGTTGGCG AGGCCTTCGG TGTGACGGCG GATGCGACGC CGCTTCTGGT CGACGAACGG    840
CGCCGCGAAC TGAACATGAT CTTCAATTTC GACGCCGTGC GCATCGGCCG TGGCGAGACC    900
TGGCACACTA GCCTTGGGC CCTGCCGGAA CTTAAGGCGA TCTATGCCCG TCTGGACGCT    960
GCGACCGACC AGCACTGCTG GGTACGGTC TTTCTCTCCA ACCACGACAA TCCTCGTCTC    1020
GTCTCCCGGT TCGGTGATGA TCATCCTGAC TGGCGGGTGG CGTCGGCCAA GGTTCTTGCC    1080
ACACTTCTCC TAACGCTGAA GGGCACGCCT TTCATCTACC AAGGCGATGA ATTGGGCATG    1140
ACCAACTATC CTCGGCTCGG TCAGGAGAC GACGATATCG AGGTGCGCAA CGCCTGGCAG    1200
GCTGAGGTCA TGACCGGTAA GGCGGATGCA GCCGAATTTC TCGGGGAGAT GCTGAAGATT    1260
TCCCGCGATC ATTCCCGCAC ACCGATGCAA TGGGACGCCA GTCTCGACGG TGGTTTCACT    1320
CGGGGTGAAA AGCCCTGGCT ATCGGTCAAT CCGAACTATC GGGCGATCAA TGCGGATGCG    1380
GCACTCGCCG ATCCCGATTC GATCTACCAT TATTACGCCG CACTCATCCG TTTCCGGCGC    1440
GAGACACCGG CGCTCATCTA CGGCGATTAT GACGACTTGG CGCCGGATCA TCCGCACCTC    1500
TTCGTCTATA CAAGAACATT GGGGTCCGAG CGCTATCTGG TCGCGCTTAA CTTCTCCGGC    1560
GATGCGCAGG CACTTGTTCT CCCGACAGAC CTGAGCGCCG CGTCACCTGT TATCGGGCGC    1620
GCCCCGCAAG TGGACCGCAT GCAGCATGAT GCTGCACGGA TCGAGCTGAT GGGTTGGGAA    1680
GCGCGGGTCT ACCACTGCGC ATGA                                          1704
```

(2) INFORMATION FOR SEQ ID NO: 16:

(i) SEQUENCE CHARACTERISTICS:
        (A) LENGTH: 567 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 16:

```
Met Thr Glu Lys Leu Ser Phe Glu Ser Thr Thr Ile Ser Arg Arg Trp
1               5                   10                  15

Trp Lys Glu Ala Val Val Tyr Gln Val Tyr Pro Arg Ser Phe Gln Asp
                20                  25                  30

Ser Asn Gly Asp Gly Ile Gly Asp Leu Pro Gly Ile Thr Ala Arg Leu
            35                  40                  45

Asp Tyr Ile Leu Gly Leu Gly Val Ser Val Ile Trp Leu Ser Pro His
        50                  55                  60

Phe Asp Ser Pro Asn Ala Asp Asn Gly Tyr Asp Ile Arg Asp Tyr Arg
65                  70                  75                  80

Lys Val Met Arg Glu Phe Gly Thr Met Ala Asp Phe Asp His Leu Leu
                85                  90                  95

Ala Glu Thr Lys Lys Arg Gly Met Arg Leu Ile Ile Asp Leu Val Val
                100                 105                 110
```

```
Asn His Thr Ser Asp Glu His Val Trp Phe Ala Glu Ser Arg Ala Ser
        115                 120                 125

Lys Asn Ser Pro Tyr Arg Asp Tyr Tyr Ile Trp His Pro Gly Arg Asp
    130                 135                 140

Gly Ala Glu Pro Asn Asp Trp Arg Ser Phe Phe Ser Gly Ser Ala Trp
145                 150                 155                 160

Thr Phe Asp Gln Pro Thr Gly Glu Tyr Tyr Met His Leu Phe Ala Asp
                165                 170                 175

Lys Gln Pro Asp Ile Asn Trp Asp Asn Pro Ala Val Arg Ala Asp Val
            180                 185                 190

Tyr Asp Ile Met Arg Phe Trp Leu Asp Lys Gly Val Asp Gly Phe Arg
        195                 200                 205

Met Asp Val Ile Pro Phe Ile Ser Lys Gln Asp Gly Leu Pro Asp Tyr
    210                 215                 220

Pro Asp His His Arg Gly Ala Pro Gln Phe Phe His Gly Ser Gly Pro
225                 230                 235                 240

Arg Leu His Asp Tyr Leu Gln Glu Met Asn Arg Glu Val Leu Ser His
                245                 250                 255

Tyr Asp Val Met Thr Val Gly Glu Ala Phe Gly Val Thr Ala Asp Ala
            260                 265                 270

Thr Pro Leu Leu Val Asp Glu Arg Arg Glu Leu Asn Met Ile Phe
        275                 280                 285

Asn Phe Asp Ala Val Arg Ile Gly Arg Gly Glu Thr Trp His Thr Lys
290                 295                 300

Pro Trp Ala Leu Pro Glu Leu Lys Ala Ile Tyr Ala Arg Leu Asp Ala
305                 310                 315                 320

Ala Thr Asp Gln His Cys Trp Gly Thr Val Phe Leu Ser Asn His Asp
                325                 330                 335

Asn Pro Arg Leu Val Ser Arg Phe Gly Asp Asp His Pro Asp Trp Arg
            340                 345                 350

Val Ala Ser Ala Lys Val Leu Ala Thr Leu Leu Thr Leu Lys Gly
        355                 360                 365

Thr Pro Phe Ile Tyr Gln Gly Asp Glu Leu Gly Met Thr Asn Tyr Pro
        370                 375                 380

Arg Leu Gly Arg Gly Asp Asp Ile Glu Val Arg Asn Ala Trp Gln
385                 390                 395                 400

Ala Glu Val Met Thr Gly Lys Ala Asp Ala Glu Phe Lys Gly Glu
                405                 410                 415

Met Leu Lys Ile Ser Arg Asp His Ser Arg Thr Pro Met Gln Trp Asp
            420                 425                 430

Ala Ser Leu Asp Gly Gly Phe Thr Arg Gly Glu Lys Pro Trp Leu Ser
        435                 440                 445

Val Asn Pro Asn Tyr Arg Ala Ile Asn Ala Asp Ala Ala Leu Ala Asp
450                 455                 460

Pro Asp Ser Ile Tyr His Tyr Ala Ala Leu Ile Arg Phe Arg Arg
465                 470                 475                 480

Glu Thr Pro Ala Leu Ile Tyr Gly Asp Tyr Asp Leu Ala Pro Asp
                485                 490                 495

His Pro His Leu Phe Val Tyr Thr Arg Thr Leu Gly Ser Glu Arg Tyr
            500                 505                 510

Leu Val Ala Leu Asn Phe Ser Gly Asp Ala Gln Ala Leu Val Leu Pro
        515                 520                 525

Thr Asp Leu Ser Ala Ala Ser Pro Val Ile Gly Arg Ala Pro Gln Val
```

|     |     | 530 |     |     | 535 |     |     | 540 |     |     |     |
| --- | --- | --- | --- | --- | --- | --- | --- | --- | --- | --- | --- |
| Asp | Arg | Met | Gln | His | Asp | Ala | Ala | Arg | Ile | Glu | Leu | Met | Gly | Trp | Glu |
| 545 |     |     |     | 550 |     |     |     | 555 |     |     |     | 560 |

Ala Arg Val Tyr His Cys Ala
               565

(2) INFORMATION FOR SEQ ID NO: 17:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (geonomic)

(xi) SEQUENCE DESCRIPTION: SEQ ID NO: 17:

TGGTGGAARG ARGCTGT                                                    17

(2) INFORMATION FOR SEQ ID NO: 18:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (geonomic)

(xi) SEQUENCE DESCRIPTION: SEQ ID NO: 18:

TCCCAGTTCA GRTCCGGCTG                                                 20

(2) INFORMATION FOR SEQ ID NO: 19:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (geonomic)

(xi) SEQUENCE DESCRIPTION: SEQ ID NO: 19:

AAAGATGGCG KCGAAAAGA                                                  19

(2) INFORMATION FOR SEQ ID NO: 20:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (geonomic)

(xi) SEQUENCE DESCRIPTION: SEQ ID NO: 20:

TGGAATGCCT TYTTCTT                                                    17

(2) INFORMATION FOR SEQ ID NO: 21:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (geonomic)

(xi) SEQUENCE DESCRIPTION: SEQ ID NO: 21:

ATCCCGAAGT GGTGGAAGGA GGC                                        23

(2) INFORMATION FOR SEQ ID NO: 22:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (geonomic)

(xi) SEQUENCE DESCRIPTION: SEQ ID NO: 22:

CGGAATTCTT ATGCCCCGTC AAGGA                                      25

(2) INFORMATION FOR SEQ ID NO: 23:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (geonomic)

(xi) SEQUENCE DESCRIPTION: SEQ ID NO: 23:

TGGTGGAAAG AAGCTGT                                               17

(2) INFORMATION FOR SEQ ID NO: 24:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (geonomic)

(xi) SEQUENCE DESCRIPTION: SEQ ID NO: 24:

TCCCAGTTCA GGTCCGGCTG                                            20

(2) INFORMATION FOR SEQ ID NO: 25:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (geonomic)

(xi) SEQUENCE DESCRIPTION: SEQ ID NO: 25:

CARTTYGGYT AYGG                                                  14

(2) INFORMATION FOR SEQ ID NO: 26:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (geonomic)

(xi) SEQUENCE DESCRIPTION: SEQ ID NO: 26:

GTTTTCCCAG TCACGAC                                               17